(12) United States Patent
Chang et al.

(10) Patent No.: US 10,100,308 B2
(45) Date of Patent: *Oct. 16, 2018

(54) METHOD FOR SELECTIVELY INHIBITING ACAT1 IN THE TREATMENT OF NEURODEGENERATIVE DISEASES

(71) Applicant: Trustees of Dartmouth College, Hanover, NH (US)

(72) Inventors: Ta-Yuan Chang, Etna, NH (US); Catherine C. Y. Chang, Etna, NH (US); Yohei Shibuya, West Lebanon, NH (US); Zhaoyang Niu, Hanover, NH (US)

(73) Assignee: Trustees of Dartmouth College, Hanover, NH (US)

(*) Notice: Subject to any disclaimer, the term of this patent is extended or adjusted under 35 U.S.C. 154(b) by 25 days.

This patent is subject to a terminal disclaimer.

(21) Appl. No.: 15/313,642

(22) PCT Filed: May 28, 2015

(86) PCT No.: PCT/US2015/032908
§ 371 (c)(1),
(2) Date: Nov. 23, 2016

(87) PCT Pub. No.: WO2015/184105
PCT Pub. Date: Dec. 3, 2015

(65) Prior Publication Data
US 2017/0292128 A1 Oct. 12, 2017

Related U.S. Application Data

(63) Continuation of application No. 14/550,025, filed on Nov. 21, 2014, now Pat. No. 9,388,414, and a continuation of application No. 14/289,996, filed on May 29, 2014, now Pat. No. 9,388,413.

(51) Int. Cl.
| | | |
|---|---|---|
| *A61P 25/28* | (2006.01) |
| *C12N 15/113* | (2010.01) |
| *C12N 7/00* | (2006.01) |
| *A61K 31/44* | (2006.01) |
| *A61K 31/255* | (2006.01) |
| *A61K 48/00* | (2006.01) |

(52) U.S. Cl.
CPC ........ *C12N 15/1137* (2013.01); *A61K 31/255* (2013.01); *A61K 31/44* (2013.01); *C12N 7/00* (2013.01); *C12Y 203/01009* (2013.01); *A61K 48/00* (2013.01); *C12N 2310/14* (2013.01); *C12N 2310/141* (2013.01); *C12N 2710/10043* (2013.01); *C12N 2710/10071* (2013.01)

(58) Field of Classification Search
CPC ... A61K 31/165; A61K 31/496; C12N 15/137
USPC ..... 435/6.1, 91.1, 91.31, 455, 458; 514/1, 2, 514/44; 536/23.1, 24.5; 424/9.1; 515/1, 515/2, 312, 346, 348, 517
See application file for complete search history.

(56) References Cited

U.S. PATENT DOCUMENTS

| | | | | |
|---|---|---|---|---|
| 8,466,121 | B2 | 6/2013 | Chang et al. | 514/44 R |
| 8,802,646 | B2 | 8/2014 | Chang et al. | 435/6.16 |
| 9,149,492 | B2* | 10/2015 | Chang | A61K 9/5184 |
| 9,388,413 | B2* | 7/2016 | Chang | C12N 15/1137 |
| 9,388,414 | B2* | 7/2016 | Chang | A61K 31/167 |
| 2005/0118226 | A1 | 6/2005 | Kovacs et al. | 424/423 |
| 2007/0087363 | A1 | 4/2007 | Bartel et al. | 435/6 |
| 2008/0177045 | A1 | 7/2008 | Lee et al. | 530/388.1 |
| 2009/0004668 | A1 | 1/2009 | Chen et al. | 435/6.14 |
| 2014/0044757 | A1 | 2/2014 | Chang et al. | 424/400 |
| 2014/0308340 | A1 | 10/2014 | Chang et al. | 424/450 |

FOREIGN PATENT DOCUMENTS

WO   WO 02/44321   6/2002

OTHER PUBLICATIONS

Agrawal, S. and Kandimalla, E. R. "Antisense Therapeutics: Is it as Simple as Complementary Base Recognition?" Molecular Medicine Today 2000 6(2):72-81.
Alvarez-Erviti et al. "Delivery of SiRNA to the Mouse Brain by Systemic Injection of Targeted Exosomes" Nature Biotechnology 2011 29(4):341-345.
Beaven, S. W. and Tontonoz, P. "Nuclear Receptors in Lipid Metabolism: Targeting the Heart of Dyslipidemia" Annual Review of Medicine 2006 57:313-329.
Björkhem I. "Crossing the Barrier: Oxysterols as Cholesterol Transporters and Metabolic Modulators in the Brain" Journal of Internal Medicine 2006 260:493-508.
Björkhem, I. "Are Side-chain Oxidized Oxysterols Regulators Also in vivo?" Journal of Lipid Research 2009 50:S213-S218.
Brown et al. "Differential Expression of Cholesterol Hydroxylases in Alzheimer's Disease" The Journal of Biological Chemistry 2004 279(33):34674-34681.
Caccamo et al. "Molecular Interplay between Mammalian Target of Rapamycin (mTOR), Amyloid-β, and Tau: Effects on Cognitive Impairments" The Journal of Biological Chemistry 2010 285(17):13107-13120.
Chang et al. "Immunological Quantitation and Localization of ACAT-1 and ACAT-2 in Human Liver and Small Intestine" The Journal of Biological Chemistry 2000 275(36):28083-28092.
Chang et al. "Acyl-Coenzyme A:Cholesterol Acyltransferases" American Journal of Physiology—Endocrinology and Metabolism 2009 297:E1-E9.
Chirila et al. "The Use of Synthetic Polymers for Delivery of Therapeutic Antisense Oligodeoxynucleotides" Biomaterials 2002 23(2):321-342.

(Continued)

*Primary Examiner* — Jane J Zara
(74) *Attorney, Agent, or Firm* — Licata & Tyrrell P.C.

(57) ABSTRACT

The present invention features methods for stimulating clearance of misfolded or aggregated proteins or peptides in microglia or neurons, and treating neurodegenerative diseases associated with such pathology in brain by selectively inhibiting the expression or activity of Acyl-CoA: Cholesterol Acyltransferase 1, but not Acyl-CoA: Cholesterol Acyltransferase 2.

16 Claims, 5 Drawing Sheets
Specification includes a Sequence Listing.

(56) References Cited

OTHER PUBLICATIONS

Chow et al. "Toll-Like Receptor-4 Mediates Lipopolysaccharide-Induced Signal Transduction" The Journal of Biological Chemistry 1999 274(16):10689-10692.

Crooke, S. T. "Progress in Antisense Technology" Annual Review of Medicine 2004 55:61-95.

Dietschy, J. M. and Turley, S. D. "Cholesterol Metabolism in the Central Nervous System During Early Development and in the Mature Animal" Journal of Lipid Research 2004 45:1375-1397.

Doench et al. "siRNAs Can Function as miRNAs" Genes & Development 2003 17:438-442.

Giovannoni et al. "Selective ACAT Inhibitors as Promising Antihyperlipidemic, Antiatherosclerotic and Anti-Alzheimer Drugs" Mini Reviews in Medicinal Chemistry 2003 3:576-584.

Goldstein et al. "Protein Sensors for Membrane Sterols" Cell 2006 124:35-46.

Halford, R. W. and Russell, D. W. "Reduction of Cholesterol Synthesis in the Mouse Brain Does Not Affect Amyloid Formation in Alzheimer's Disease, but Does Extend Lifespan" Proceedings of the National Academy of Sciences 2009 106(9):3502-3506.

Hartmann, T. "Cholesterol, Aβ and Alzheimer's Disease" Trends in Neuroscience 2001 24(11):S45-S48.

Heverin et al. "Changes in the Levels of Cerebral and Extracerebral Sterols in the Brain of Patients with Alzheimer's Disease" Journal of Lipid Research 2004 45:186-193.

Holen et al. "Positional Effects of Short Interfering RNAs Targeting the Human Coagulation Trigger Tissue Factor" Nucleic Acids Research 2002 30(8):1757-1766.

Hudry et al. "Adeno-associated Virus Gene Therapy with Cholesterol 24-Hydroxylase Reduces the Amyloid Pathology Before or After the Onset of Amyloid Plaques in Mouse Models of Alzheimer's Disease" Molecular Therapy 2010 18(1):44-53.

Hutter-Paier et al. "The ACAT Inhibitor CP-113, 818 Markedly Reduces Amyloid Pathology in a Mouse Model of Alzheimer's Disease" Neuron 2004 44:227-238.

Huttunen, H. J. and Kovacs, D. M. "ACAT as a Drug Target for Alzheimer's Disease" Neurodegenerative Diseases 2008 5:212-214.

Huttunen et al. "Knockdown of ACAT-1 Reduces Amyloidogenic Processing of APP" FEBS Letters 2007 581:1688-1692.

Ikenoya et al. "A Selective ACAT-1 Inhibitor, K-604, Suppresses Fatty Streak Lesions in Fat-fed Hamsters without Affecting Plasma Cholesterol Levels" Atherosclerosis 2007 191:290-297.

Jiang et al. " ApoE Promotes the Proteolytic Degradation of Aβ" Neuron 2008 58:681-693.

Karu et al. "Liquid Chromatography-Mass Spectrometry Utilizing Multi-Stage Fragmentation for the Identification of Oxysterols" Journal of Lipid Research 2007 48:976-987.

Koffie et al. "Oligomeric Amyloid β Associates with Postsynaptic Densities and Correlates with Excitatory Synapse Loss Near Senile Plaques" Proceedings of the National Academy of Sciences 2009 106(10):4012-4017.

Kotti et al. "Brain Cholesterol Turnover Required for Geranylgeraniol Production and Learning in Mice" Proceedings of the National Academy of Sciences 2006 103(10):3869-3874.

Lesné et al. "A Specific Amyloid-β Protein Assembly in the Brain Impairs Memory" Nature 2006 440(16):352-357.

Lublin, A. L. and Gandy, S. "Amyloid-β Oligomers: Possible Roles as Key Neurotoxins in Alzheimer's Disease" Mount Sinai Journal of Medicine 2010 77:43-49.

Lund et al. "Knockout of the Cholesterol 24-Hydroxylase Gene in Mice Reveals a Brain-specific Mechanism of Cholesterol Turnover" The Journal of Biological Chemistry 2003 278(25):22980-22988.

Lütjohann et al. "Cholesterol Homeostasis in Human Brain: Evidence for an Age-Dependent Flux of 24S-Hydroxycholesterol from the Brain into the Circulation" Proceedings of the National Academy of Sciences 1996 93:9799-9804.

Martins et al. "Lipids Revert Inert Aβ Amyloid Fibrils to Neurotoxic Protofibrils that Affect Learning in Mice" The EMBO Journal 2008 27:224-233.

Masters, C. L. and Selkoe, D. J. "Biochemistry of Amyloid β-Protein and Amyloid Deposits in Alzheimer Disease" Cold Spring Harbor Perspectives in Medicine 2012 A006262.

Mizushima, N. "Autophagy: Process and Function" Genes & Development 2007 21:2861-2873.

Mizushima et al. "Autophagy Fights Disease through Cellular Self-Digestion" Nature 2008 451(7182):1069-1075.

Opalinska, J. B. and Gewirtz, A. M. "Nucleic-acid Therapeutics: Basic Principles and Recent Applications" Nature Reviews Drug Discovery 2002 1(7):503-514.

Pardridge, W. M. "shRNA and siRNA Delivery to the Brain" Advanced Drug Delivery Reviews 2007 59(2-3):141-152.

Peracchi, A. "Prospects for Antiviral Ribozymes and Deoxyribozymes" Reviews in Medical Virology 2004 14(1):47-64.

Puglielli et al. "Acyl-Coenzyme A: Cholesterol Acyltransferase Modulates the Generation of the Amyloid β-Peptide" Nature Cell Biology 2001 3:905-912.

Pulford et al. "Liposome-siRNA-Peptide Complexes Cross the Blood-Brain Barrier and Significantly Decrease $PrP^C$ on Neuronal Cells and $PrP^{RES}$ in Infected Cell Cultures" PLoS ONE 2010 5(6):e11085.

Repa, J. J. and Mangelsdorf, D. J. "The Role of Orphan Nuclear Receptors in the Regulation of Cholesterol Homeostasis" Annual Review of Cell and Developmental Biology 2000 16:459-481.

Russell et al. "Cholesterol 24-Hydroxylase: An Enzyme of Cholesterol Turnover in the Brain" Annual Review of Biochemistry 2009 78:1017-1040.

Sardiello et al. "A Gene Network Regulating Lysosomal Biogenesis and Function" Science 2009 325:473-477.

Scheek et al. "Sphingomyelin Depletion in Cultured Cells Blocks Proteolysis of Sterol Regulatory Element Binding Proteins at Site 1" Proceedings of the National Academy of Sciences 1997 94:11179-11183.

Settembre et al. "TFEB Links Autophagy to Lysosomal Biogenesis" Science 2011 332(6036):1429-1433.

Settembre et al. "A Lysosome-to-Nucleus Signalling Mechanism Senses and Regulates the Lysosome via mTOR and TFEB" The EMBO Journal 2012 31(5):1095-1108.

Shankar et al. "Amyloid β-Protein Dimers Isolated Directly from Alzheimer Brains Impair Synaptic Plasticity and Memory" Nature Medicine 2008 14(8):837-842.

Song et al. "Insig-Mediated Degradation of HMG CoA Reductase Stimulated by Ianosterol, an Intermediate in the Synthesis of Cholesterol" Cell Metabolism 2005 1:179-189.

Spilman et al. "Inhibition of mTOR by Rapamycin Abolishes Cognitive Deficits and Reduces Amyloid-β Levels in a Mouse Model of Alzheimer's Disease" PLoS ONE 2010 5(4):e9979.

Tabas et al. "Inhibition of Acyl Coenzyme A: Cholesterol Acyl Transferase in J774 Macrophages Enhances Down-regulation of the Low Density Lipoprotein Receptor and 3-Hydroxy-3-methylglutaryl-Coenzyme A Reductase and Prevents Low Density Lipoprotein-induced Cholesterol Accumulation" The Journal of Biological Chemistry 1986 261(7):3147-3155.

Tarr, P. T. and Edwards, P. A. "ABCG1 and ABCG4 are Coexpressed in Neurons and Astrocytes of the CNS and Regulate Cholesterol Homeostasis through SREBP-2" Journal of Lipid Research 2008 49:169-182.

Wang et al. "ATP-Binding Cassette Transporters G1 and G4 Mediate Choleseterol and Desmosterol Efflux to HDL and Regulate Sterol Accumulation in the Brain" The FASEB Journal 2008 22:1073-1082.

Wang et al. "The Effect of 24S-Hydroxycholesterol on Cholesterol Homeostasis in Neurons: Quantitative Changes to the Cortical Neuron Proteome" Journal of Proteome Research 2008 7(4):1606-1614.

Wellington, C. L. "Cholesterol at the Crossroads: Alzheimer's Disease and Lipid Metabolism" Clinical Genetics 2004 66:1-16.

Wolozin, B. "Cholesterol and the Biology of Alzheimer's Disease" Neuron 2004 41:7-10.

Zhou et al. "Activation of Lysosomal Function in the Course of Autophagy via mTORC1 Suppression and Autophagosome-Lysosome Fusion" Cell Research 2013 23:508-523.

(56) References Cited

OTHER PUBLICATIONS

Zhuang et al. "Treatment of Brain Inflammatory Diseases by Delivering Exosome Encapsulated Anti-Inflammatory Drugs from the Nasal Region to the Brain" Molecular Therapy 2011 19(10):1769-1779.
Office communication dated Jul. 24, 2012 from U.S. Appl. No. 13/072,915, filed Mar. 28, 2011.
Office communication dated Dec. 11, 2013 from U.S. Appl. No. 13/605,206, filed Sep. 6, 2012.
International Search Report from PCT/US2009/056607, dated Feb. 4, 2010, PCT.
International Preliminary Report on Patentability from PCT/US2009/056607, dated Apr. 21, 2011, PCT.
Office communication dated Nov. 9, 2015 from U.S. Appl. No. 14/289,996, filed May 29, 2014.
Office communication dated Feb. 23, 2016 from U.S. Appl. No. 14/289,996, filed May 29, 2014.
Office communication dated Mar. 23, 2016 from U.S. Appl. No. 14/289,996, filed May 29, 2014.
Office communication dated Nov. 6, 2015 from U.S. Appl. No. 14/550,025, filed Nov. 21, 2014.
Office communication dated Feb. 23, 2016 from U.S. Appl. No. 14/550,025, filed Nov. 21, 2014.
Office communication dated Apr. 6, 2016 from U.S. Appl. No. 14/550,025, filed Nov. 21, 2014.

\* cited by examiner

SEQUENCE LISTING

```
<160> NUMBER OF SEQ ID NOS: 46

<210> SEQ ID NO 1
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 1
agcccagaaa aatttcatgg acacatacag                                    30

<210> SEQ ID NO 2
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 2
cccttgttct ggaggtgctc tcagatcttt                                    30

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
tttgctctat gcctgcttca                                               20

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide
```

```
<400> SEQUENCE: 4
ccatgaagag aaaggtccac a                                              21

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 5
atggtgaagg tcggtgtg                                                  18

<210> SEQ ID NO 6
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 6
cattctcggc cttgactg                                                  18

<210> SEQ ID NO 7
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 7
acggcgctga aggagatc                                                  18

<210> SEQ ID NO 8
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 8
gtccagggcc atcttgac                                                  18

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
cccactgatg gtaatgctgg c                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
ggaatcacaa agtggggatg g                                              21

<210> SEQ ID NO 11
<211> LENGTH: 28
```

```
<212> TYPE: DNA
<213> ORGANISM: Artificial Sequence
<220> FEATURE:
<223> OTHER INFORMATION: Synthetic oligonucleotide

<400> SEQUENCE: 11
ggtttggaga tggttataca atagttgt                                            28

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 12
ttcccggaaa cgcaagtc                                                       18

<210> SEQ ID NO 13
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 13
aggtctcagc cttctaaagt tcctc                                               25

<210> SEQ ID NO 14
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 14
tctctcgaag tgaatgaaat ttatcg                                              26

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
ctgtcctatt ccgtgcggga                                                     20

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
gggacttcat gagggacacc actt                                                24

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
```
agccaatagt ggaagacatg ca                                              22

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 18
gcaggacagg agaaggatac tcat                                            24

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
cagtgaaggt catgctggag                                                 20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
cgcaatgaag aaggtgacaa                                                 20

<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 21
tctggcagtc agtgggaact att                                             23

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 22
cctcgtcctt cgatccaatt t                                               21

<210> SEQ ID NO 23
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 23
gccgtcaact gggtcgaa                                                   18

<210> SEQ ID NO 24
<211> LENGTH: 24
<212> TYPE: DNA
<213> ORGANISM: Artificial Sequence

```
<220> FEATURE:
<223> OTHER INFORMATION: Synthetic oligonucleotide

<400> SEQUENCE: 24
gcatatatag caatgtctcc tgca                                              24

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 25
ttgctcgaga tgtcatgaag ga                                                22

<210> SEQ ID NO 26
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 26
agcaggtcag caaagaactt atagc                                             25

<210> SEQ ID NO 27
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 27
ctgtgggctc cataggctat ct                                                22

<210> SEQ ID NO 28
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 28
gcggtccagg gtcatcttc                                                    19

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
tgggtctccc gaaatctgtt                                                   20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
accaccgcat tcttgaagga                                                   20
```

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
aaccagaagc tcaagcagga                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
tcatgccctc catagacaca                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
gtggagcagt ctcaacgtca                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
tggtaggtct cacccaggag                                               20

<210> SEQ ID NO 35
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 35
ccaactcaat gggtctgttc ct                                            22

<210> SEQ ID NO 36
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 36
tggcttagca aagtcttcca act                                           23

<210> SEQ ID NO 37
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 37
ggagctgaag ccactattta t                                              21

<210> SEQ ID NO 38
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 38
ctgtttgaag tggaccacat ca                                             22

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 39
cccggttcat tctgatactg ga                                             22

<210> SEQ ID NO 40
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 40
aactacccaa ggactcctac tgta                                           24

<210> SEQ ID NO 41
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 41
tgctgtccag tatcagaatg aaccgggttt tggccactga ctgacccggt tcactgatac    60
tgga                                                                 64

<210> SEQ ID NO 42
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 42
tgctgtacag taggagtcct tgggtagttt tggccactga ctgactaccc aagctcctac    60
tgta                                                                 64

<210> SEQ ID NO 43
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 43
caugaucuuc cagauuggag uucua 25

<210> SEQ ID NO 44
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 44
uagaacucca aucuggaaga ucaug 25

<210> SEQ ID NO 45
<211> LENGTH: 29
<212> TYPE: PRT
<213> ORGANISM: Artificial sequence
<220> FEATURE:
<223> OTHER INFORMATION: Synthetic peptide

<400> SEQUENCE: 45

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
            20                  25

<210> SEQ ID NO 46
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 46
tactgcgcgt ggagacg 17

METHOD FOR SELECTIVELY INHIBITING ACAT1 IN THE TREATMENT OF NEURODEGENERATIVE DISEASES

This invention was made with government support under R01HL060306 and R01AG037609 awarded by the National Institutes of Health. The government has certain rights in the invention.

INTRODUCTION

This application is a U.S. National Stage Application of PCT/US2015/032908 filed May 28, 2015 and claims benefit of priority from U.S. patent application Ser. No. 14/550,025 filed Nov. 21, 2014 and Ser. No. 14/289,996 filed May 29, 2014, the contents of each of which are incorporated herein by reference in their entirety.

BACKGROUND

Alzheimer's disease is the most common form of dementia in the aging population. In Alzheimer's disease, an important biochemical characteristic is the extracellular accumulation of amyloid β (Aβ), especially Aβ1-42, to form the insoluble amyloid plaques in brain tissue of Alzheimer's patients. Aβ is produced by proteolytic cleavages of amyloid precursor protein (APP) (Masters & Selkoe (2012) *Cold Spring Harb. Perspect. Med.* A006262). Recent evidence indicates that the size of the amyloid plaques, which mainly consist of aggregates of the fibrillar form of Aβ, does not correlate well with the degree of neurodegeneration or the severity of dementia in Alzheimer's disease (Lublin and Gandy. 2010. *Mt. Sinai J. Med. Transl. Pers. Med.* 77:43-49). Instead, the oligomeric forms of Aβ, which are intermediate forms between the monomeric and the fibrillar forms, have been suggested to be the most toxic molecular species that cause synaptic loss (Koffie et al. (2009) *Proc. Natl. Acad. Sci. USA* 106:4012-4017; Lesne et al. (2006) *Nature* 440:352-357; Martins et al. (2008) *EMBO J.* 27:224-233; Shankar et al. (2008) *Nat. Med.* 14:837-842).

Studies have shown that cholesterol content in cells can affect the production of Aβ, in part by the ability of cholesterol to modulate the enzyme activities of various secretases in cell membranes (Wolozin (2004) *Neuron* 41:7-10). Cholesterol metabolism has also been implicated in the pathogenesis of Alzheimer's disease in other manners (Jiang et al. (2008) *Neuron* 58:681-693; Wellington (2004) *Clin. Genet.* 66:1-16; Hartmann (2001) *Trends Neurosci.* 24:S45-48).

In the brain, cholesterol is derived from endogenous biosynthesis (Dietschy & Turley (2004) *J. Lipid Res.* 45:1375-1397). The transcription factor SREBP2 controls the expression of enzymes involved in cholesterol biosynthesis, including the rate-limiting enzyme HMG-CoA reductase (HMGR) (Goldstein et al. (2006) *Cell* 124:35-46). Other transcription factors, including liver X receptors (LXRs), control the expression of proteins which function in cholesterol transport (Repa & Mangelsdorf (2000) *Annu. Rev. Cell Dev. Biol.* 16:459-481; Beaven & Tontonoz. (2006) *Annu. Rev. Med.* 57:313-329), including apoE, ABCA1, and others (Wang, et al. (2008) *FASEB J.* 22:1073-1082; Tarr & Edwards (2008) *J. Lipid Res.* 49:169-182). In the brain, cholesterol can be enzymatically converted by a brain-specific enzyme, 24-hydroxylase (CYP46A1) (Russell et al. (2009) *Annu. Rev. Biochem.* 78:1017-1040), to an oxysterol called 24S-hydroxycholesterol (24SOH); the concentration of 24SOH far exceeds those of other oxysterols in the brain (Lutjohann et al. (1996) *Proc. Natl. Acad. Sci. USA* 93:9799-9804; Bjorkhem. (2006) *J. Intern. Med.* 260:493-508; Karu et al. (2007) *J. Lipid Res.* 48:976-987). Various oxysterols, including 24SOH, can down-regulate sterol synthesis in intact cells and in vitro (Song et al. (2005) *Cell Metab.* 1:179-189; Wang et al. (2008) *J. Proteome Res.* 7:1606-1614). When provided to neurons, 24SOH decreases the secretion of Aβ (Brown et al. (2004) *J. Biol. Chem.* 279: 34674-34681). However, whether 24SOH or other oxysterols can act in similar fashion(s) in vivo remains to be demonstrated. 24SOH levels have been shown to be decreased in brain samples from Alzheimer's disease patients (Heverin et al. (2004) *J. Lipid Res.* 45:186-193), suggesting a relationship between 24SOH and Alzheimer's disease.

Acyl-CoA: Cholesterol Acyltransferase (ACAT) converts free cholesterol to cholesterol ester, and is one of the key enzymes in cellular cholesterol metabolism. Two ACAT genes have been identified which encode two different enzymes, ACAT1 and ACAT2 (also known as SOAT1 and SOAT2). ACAT1 and ACAT2 have different tissue expression patterns (Chang et al. (2009) *Am. J. Physiol. Endocrinol. Metab.* 297:E1-E9). ACAT1 is a resident enzyme in the endoplasmic reticulum and is ubiquitously expressed in all tissues examined, while ACAT2 is expressed mainly in the intestines and liver (Chang et al. (2009) *Am. J. Physiol. Endocrinol. Metab.* 297:E1-E9). Early studies showed that in cells expressing human APP, inhibiting ACAT activity significantly reduced the amount of Aβ secreted into growth medium (Puglielli et al. (2001) *Nat. Cell Biol.* 3:905-912). Alzheimer's disease-like pathology has been demonstrated in the brains of transgenic mice expressing human APP(751) containing the London (V717I) and Swedish (K670M/N671L) mutations (Hutter-Paier, et al. (2004) *Neuron.* 44(2): 227-38). Two months of treatment with CP-113,818, a non-selective ACAT inhibitor, was shown to reduce the accumulation of amyloid plaques by 88%-99% and membrane/insoluble Amyloid β levels by 83%-96%, while also decreasing brain cholesteryl-esters by 86%. Additionally, soluble Amyloid β(42) was reduced by 34% in brain homogenates. Spatial learning was slightly improved and correlated with decreased Amyloid β levels. In nontransgenic littermates, CP-113,818 also reduced ectodomain shedding of endogenous APP in the brain. A 50% decrease in ACAT1 expression has also been shown to reduce cholesteryl ester levels by 22%, reduce proteolytic processing of APP, and decrease Amyloid β secretion by 40% (Huttunen et al. (2007) *FEBS Lett.* 581(8):1688-92) in an in vitro neuronal cell line.

Macroautophagy, or autophagy, is a conserved lysosomal degradation process that begins with sequestration of certain cytoplasmic content with a double-membrane structure, followed by formation of an autophagosome (Mizushima. (2007) *Genes Dev.* 21:2861-2873). Autophagosomes fuse with lysosomes to degrade sequestered cytoplasmic contents, including denatured and/or aggregation-prone proteins/peptides, such as Aβ (Mizushima et al. (2008) *Nature* 451:1069-1075). Autophagosome formation can be induced by inhibition of the mammalian target of rapamycin (mTOR) (Mizushima, (2007) *Genes Dev.* 21:2861-2873). Inhibition of mTOR signaling also up-regulates lysosome biogenesis and leads to efficient autophagosome-lysosome fusions (Zhou et al. (2013) *Cell Res.* 23:508-523). The transcription factor EB (TFEB), a newly discovered master regulator of lysosomal protein biogenesis (Sardiello et al. (2009) *Science* 325:473-477), coordinates these two processes by activating the autophagic machinery and by increasing the expression of lysosome-specific genes (Settembre et al. (2011) *Science* 332:1429-1433; Settembre et al. (2012) *EMBO J.* 31:1095-1108; Zhou et al. (2013) *Cell Res.* 23:508-523). In mouse models of Alzheimer's disease, studies have shown that blocking mTOR by rapamycin administration increases autophagy in the brain, reduces Aβ1-42 levels, and rescues cognitive deficits (Caccamo et al. (2010) *J. Biol. Chem.* 285:13107-13120; Spillman et al. (2010) *PLoS ONE* 5:e9979).

SUMMARY OF THE INVENTION

The present invention features methods for stimulating clearance of misfolded or aggregated proteins and peptides in microglia or neurons by administering to a subject in need thereof an Acyl-CoA: Cholesterol Acyltransferase 1-selective inhibitor thereby stimulating clearance of the misfolded or aggregated proteins and peptides in microglia or neurons in the subject. In some embodiments, the inhibitor is administered either as a naked molecule, or encapsulated within an exosome or liposome. Also contemplated by the present invention are methods for treating a neurodegenerative disease associated with accumulation of misfolded or aggregated proteins or peptides in microglia or neurons of brain tissue by administering to a subject in need thereof an exosome or liposome-encapsulated Acyl-CoA: Cholesterol Acyltransferase 1-selective inhibitor thereby decreasing the accumulation of misfolded or aggregated proteins or peptides in microglia or neurons of brain tissue in the subject, thereby treating the neurodegenerative disease. In certain instances, the methods involve treating neurodegenerative diseases that would include but not be limited to Alzheimer's disease, Parkinson's disease, tauopathy, frontotemporal dementia, Huntington disease, and amylotrophic lateral sclerosis. Variations on the methods of the instant invention feature use of Acyl-CoA: Cholesterol Acyltransferase 1, use of such inhibitors wherein the inhibitor has an $IC_{50}$ value for Acyl-CoA: Cholesterol Acyltransferase 1 which is at least twice the corresponding $IC_{50}$ value for Acyl-CoA: Cholesterol Acyltransferase 2, use of inhibitors wherein the inhibitor has an $IC_{50}$ value in the range of 1 nM to 100 μM, with or without encapsulation of the inhibitor within liposomes or exosomes, and modifying the exosome or liposome by attaching a brain-targeting moiety. In certain embodiments, the inhibitor is administered intranasally. In other embodiments, the inhibitor is administered intrathecally.

DETAILED DESCRIPTION OF THE INVENTION

Figure 1:
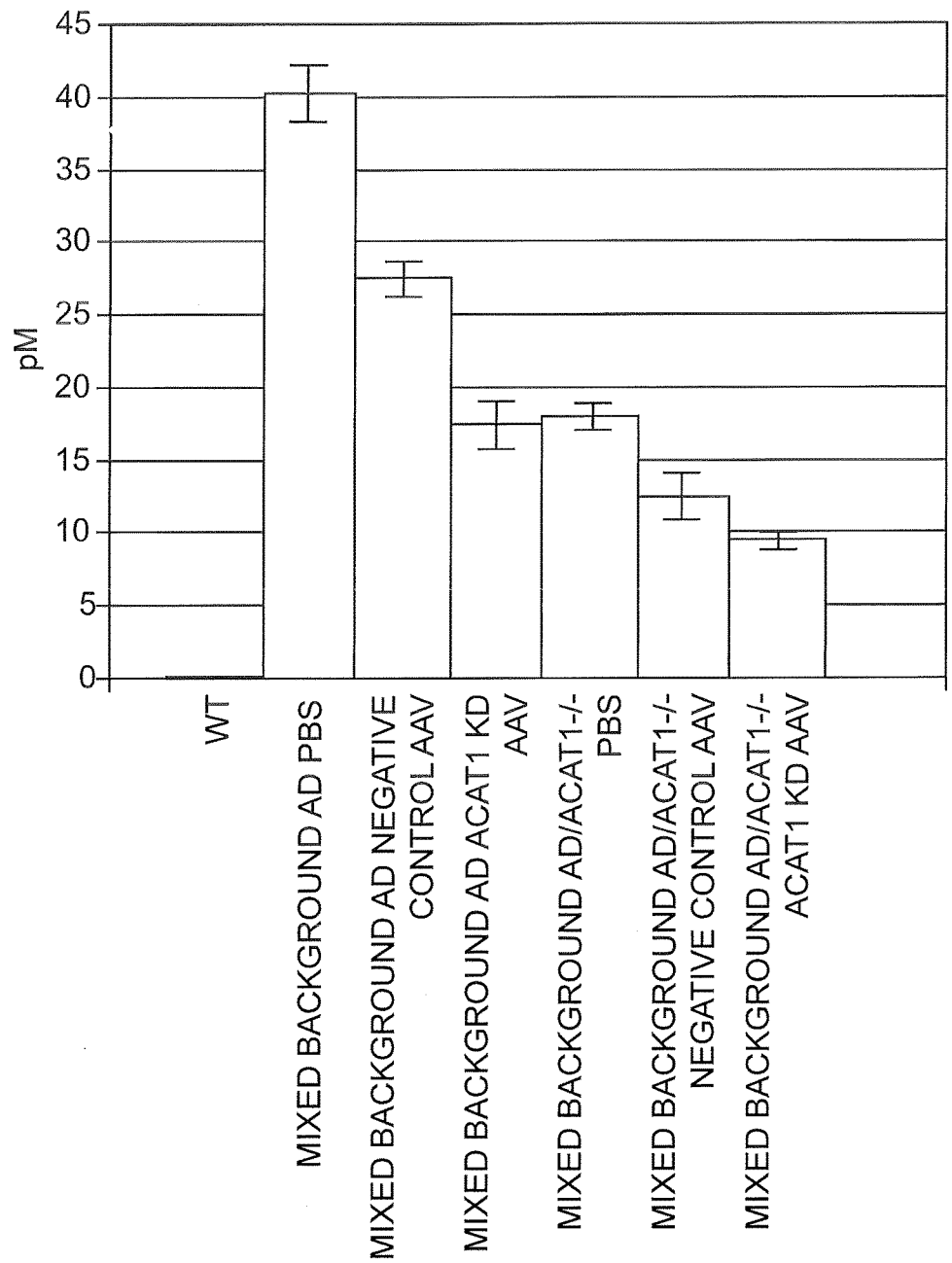
FIG. 1 shows amyloid beta 42 (Aβ1-42) levels in the hemibrains of wild-type (WT) Alzheimer's Disease (AD) mice or AD mice lacking Acat1 (Acat1$^{-/-}$) after injection of PBS, or injection with adeno-associated virus (AAV) vectors harboring a negative control miRNA or with a microRNA that contains the siRNA targeting ACAT1 (ACAT1 KD). Mice were injected at 10 months of age and analyzed at 12 months of age. Group 1, WT mice (n=1); Group 2, mixed background AD mice injected with PBS (n=6); Group 3, mixed background AD mice injected with negative control AAV (n=8); Group 4, mixed background AD mice injected with Acat1 KD AAV (n=13); Group 5, mixed background AD/Acat1$^{-/-}$ mice injected with PBS (n=9); Group 6, mixed background AD/Acat1$^{-/-}$ mice injected with negative control AAV (n=4); Group 7, mixed background AD/Acat1$^{-/-}$ mice injected with Acat1 KD AAV (n=4).

Amyloid beta-peptide (Abeta or Aβ) accumulation in specific brain regions is a pathological hallmark of Alzheimer's disease (AD). It has now been found that ACAT1, but not ACAT2, plays a significant role in amyloid pathology of AD in vivo. Specifically, ACAT1 modulates the sizes and densities of amyloid plaques and cognitive decline manifested in a mouse model for the AD in vivo. In addition, contrary to previous reports (Hutter-Paier, et al. (2004) supra), it has been shown that ACAT1 deficiency leads to decreases in hAPP, as well as its proteolytic fragments. This finding indicates that ACAT1 deficiency acts to reduce Aβ load at least in part by reducing the hAPP protein content. Furthermore, ACAT1 deficiency causes an increase in 24SOH content, a decrease in HMGR content, and a decrease in sterol biosynthesis, indicating that 24SOH is a key molecule in regulating brain sterol biosynthesis in vivo. Moreover, inhibition of ACAT1 stimulates oligomeric Aβ clearance in microglia and decreases tau in neurons. Oligomeric Aβ is derived from monomeric Aβ and is known to be much more neurotoxic than monomeric Aβ. Additional studies have shown that Acat1 gene knockout, or use of a specific ACAT1 inhibitor, stimulates autophagosome formation and lysosomal proteolysis. Unexpectedly, the effect of ACAT1 inhibition did not alter mTOR signaling or endoplasmic reticulum stress responses, even though the effects could be modulated by agents that disrupted cholesterol biosynthesis. Given that autophagy is needed to degrade misfolded proteins or peptides in cells, these data implicated ACAT1 inhibition as not only a therapeutic target for treating AD also a way to treat multiple neurodegenerative conditions or diseases whose pathology is characterized by the presence of misfolded proteins or peptides in the brain.

These combined experiments on the mechanism of ACAT1 inhibition confirm the importance of ACAT1 activity in neurodegenerative changes in brain tissue in disease conditions. It now has been found that autophagy is linked to ACAT1 inhibition. It has been shown that both lysosome volume and biogenesis are affected. It also has been shown that compounds that affect cholesterol biosynthesis can modulate the effect of ACAT1 inhibition on lysosome volume. A common event that occurs in many prevalent neurodegenerative diseases, including AD, Parkinson's disease, frontotemporal dementia, tauopathy, Huntington Disease, and ALS, is the presence of specific misfolded/aggregated proteins/peptides in certain regions of the brain (Ross & Poirier (2004) Nat. Med. 10:S10-S17). It is known that cellular clearance of misfolded/aggregated proteins/peptides in brain involves autophagy-mediated lysosomal proteolysis (Mizushima, et al. (2008) Nature 451:1069-1075). Therefore, inhibition of ACAT1 will provide a novel method for treating these diseases.

Accordingly, the present invention features compositions and methods for stimulating the clearance of misfolded/aggregated proteins/peptides in microglia and neurons, decreasing the symptoms associated with pathology that is linked to the presence of the misfolded/aggregated proteins and peptides, and treating a neurodegenerative disease that would include but not be limited to AD, tauopathy, Parkinson's disease, fronto-temporal dementia, Huntington disease, and amyotrophic lateral sclerosis (ALS). The present invention also features methods for treating AD, in particular, wherein stimulating Aβ clearance in microglia and/or decreasing tau in neurons, decreases AD-associated pathology, decreases cognitive decline, and treats AD. In accordance with the methods of this invention, a subject having, suspected of having or predisposed to have a neurodegenerative disease is administered an effective amount of an agent that selectively inhibits the expression or activity of ACAT1 (i.e., an anti-Acat1 siRNA, or an ACAT1-selective inhibitor) so that proteins or peptides are cleared from the brain, and the neurodegenerative disease is slowed, prevented or treated. In one embodiment, the disease is Alzheimer's disease and the protein or peptide is oligomeric Aβ, and the oligomeric Aβ is degraded in microglia, cognitive decline associated with amyloid pathology is decreased, and/or the progression of Alzheimer's disease is slowed or prevented, treating AD.

As used herein, a "selective inhibitor of ACAT1" or "ACAT1-selective inhibitor" is any molecular species that is an inhibitor of the ACAT1 enzyme but which fails to inhibit, or inhibits to a substantially lesser degree ACAT2. Methods for assessing the selectively of ACAT1 inhibitors are known in the art and can be based upon any conventional assay including, but not limited to the determination of the half maximal (50%) inhibitory concentration (IC) of a substance (i.e., 50% IC, or $IC_{50}$), the binding affinity of the inhibitor (i.e., $K_i$), and/or the half maximal effective concentration ($EC_{50}$) of the inhibitor for ACAT1 as compared to ACAT2. See, e.g., Lada, et al. (2004) J. Lipid Res. 45:378-386 and U.S. Pat. No. 5,968,749. ACAT1 and ACAT2 proteins that can be employed in such assays are well-known in the art and set forth, e.g., in GENBANK Accession Nos. NP_000010 (human ACAT1) and NP_005882 (human ACAT2). See also U.S. Pat. No. 5,834,283.

In particular embodiments, an ACAT1-selective inhibitor is an agent which has an $IC_{50}$ value for ACAT1 that is at least twice or, more desirably, at least three, four, five, or six times higher than the corresponding $IC_{50}$ value for ACAT2. Most desirably, an ACAT1-selective inhibitor has an $IC_{50}$ value for ACAT1 which is at least one order of magnitude or at least two orders of magnitude higher than the $IC_{50}$ value for ACAT2.

Selective inhibitors of ACAT1 activity have been described. See, e.g., inhibitors listed in Table 1. For example, Ikenoya, et al. ((2007) Atherosclerosis 191:290-297) teach that K604 has an $IC_{50}$ value of 0.45 μmol/L for human ACAT1 and 102.85 μmol/L for human ACAT2. As such K604 is 229-fold more selective for ACAT1 than ACAT2. In addition, diethyl pyrocarbonate has been shown to inhibit ACAT1 with 4-fold greater activity ($IC_{50}$=44 μM) compared to ACAT-2 ($IC_{50}$=170 μM) (Cho, et al. (2003) Biochem. Biophys. Res. Comm. 309:864-872). Ohshiro, et al. ((2007) J. Antibiotics 60:43-51) teach selective inhibition with beauveriolides I (0.6 μM vs. 20 μM) and III (0.9 μM vs. >20 μM) for ACAT1 over ACAT2. In addition, beauveriolide analogues 258, 280, 274, 285, and 301 show ACAT1-selective inhibition with $pIC_{50}$ values in the range of 6 to 7 (Tomoda & Doi (2008) Accounts Chem. Res. 41:32-39). Lada, et al. ((2004) J. Lipid Res. 45:378-386) teach a Warner-Lambert compound (designated therein as Compound 1A), and derivatives thereof (designated Compounds 1B, 1C, and 1D), which inhibit ACAT1 more efficiently than ACAT2 with $IC_{50}$ values 66- to 187-fold lower for ACAT1 than for ACAT2 (see Table 1). Moreover, Lee, et al. ((2004) Bioorg. Med. Chem. Lett. 14:3109-3112) teach methanol extracts of Saururus chinensis root that contain saucerneol B and manassantin B for inhibiting ACAT activity. Saucerneol B inhibited hACAT-1 and hACAT-2 with $IC_{50}$ values of 43.0 and 124.0 μM, respectively, whereas manassantin B inhibited hACAT-1 and hACAT-2 with $IC_{50}$ values of 82.0 μM and only 32% inhibition at 1 mM, respectively.

TABLE 1

| Inhibitor | Structure | IC$_{50}$ ACAT1 | IC$_{50}$ ACAT2 |
|---|---|---|---|
| K604 | 2-[4-[2-(benzimidazol-2-ylthio)ethyl]piperazin-1yl]-N-[2,4-bis(methylthio)-6-methyl-3-pyridyl]acetamide | 0.45 μmol/L | 102.85 μmol/L |
| Beauveriolide I | 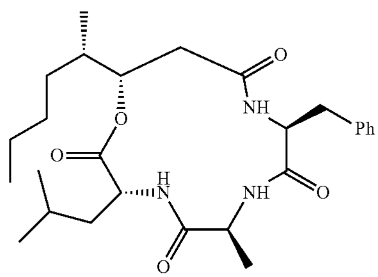 [SMILES: CCCC[C@H](C)[C@@H]1CC(=O)N[C@@H](Cc2ccccc2)C(=O)N[C@@H](C)C(=O)N[C@H](CC(C)C)C(=O)O1] | 0.6 μM | 20 μM |
| Beauveriolide III | 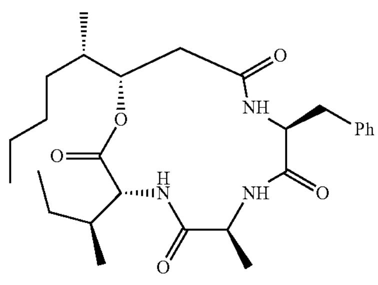 [SMILES: CCCC[C@H](C)[C@@H]1CC(=O)N[C@@H](Cc2ccccc2)C(=O)N[C@@H](C)C(=O)N[C@H]([C@@H](C)CC)C(=O)O1] | 0.9 μM | >20 μM |
| Eflucimibe (F12511) | 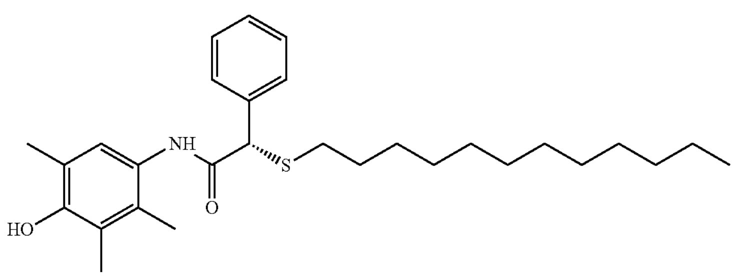 [SMILES: CCCCCCCCCCCCS[C@H](C(=O)Nc1cc(C)c(O)c(C)c1C)c1ccccc1] | 39 nM | 110 nM |
| Compound 1A | 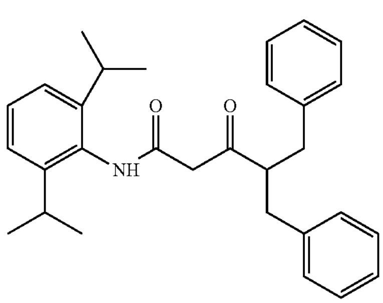 [SMILES: CC(C)c1cccc(C(C)C)c1NC(=O)CC(=O)C(Cc1ccccc1)Cc1ccccc1] | 4.2 nM | 275 nM |

TABLE 1-continued

| Inhibitor | Structure | IC$_{50}$ ACAT1 | IC$_{50}$ ACAT2 |
|---|---|---|---|
| Compound 1B | 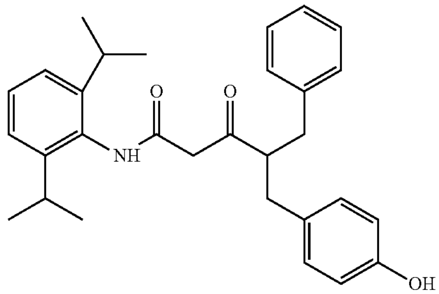 [SMILES: CC(C)c1cccc(C(C)C)c1NC(=O)CC(=O)C(Cc1ccccc1)Cc1ccc(O)cc1] | 10.3 nM | 1500 nM |
| Compound 1C | 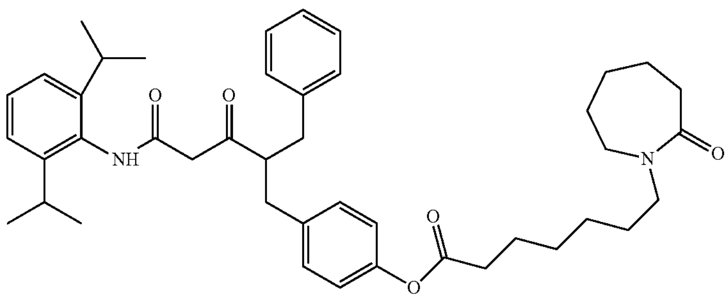 [SMILES: CC(C)c1cccc(C(C)C)c1NC(=O)CC(=O)C(Cc1ccccc1)Cc1ccc(OC(=O)CCCCCCN2CCCCCC2=O)cc1] | 3.6 nM | 530 nM |
| Compound 1D | 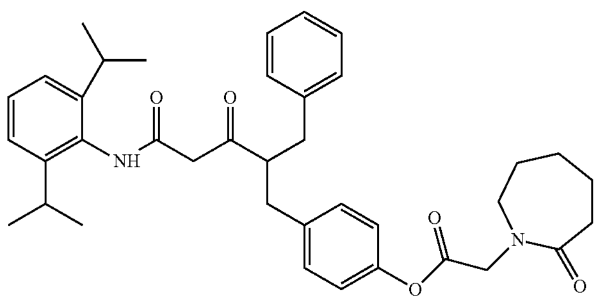 [SMILES: CC(C)c1cccc(C(C)C)c1NC(=O)CC(=O)C(Cc1ccccc1)Cc1ccc(OC(=O)CN2CCCCCC2=O)cc1] | 3.2 nM | 600 nM |
| 1$^a$ | | 61 µM | 230 µM |
| 2$^a$ | | 65 µM | 414 µM |
| 13$^a$ | | 24 µM | 53 µM |

TABLE 1-continued

| Inhibitor | Structure | IC$_{50}$ ACAT1 | ACAT2 |
|---|---|---|---|
| 14[a] | 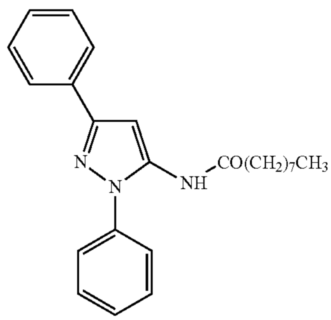 | 23 µM | 75 µM |
| 16[a] | 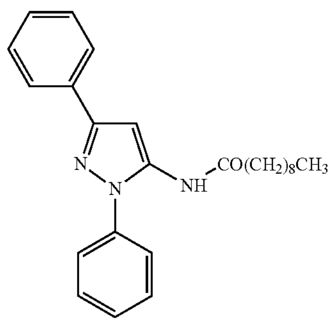 | 39 µM | 97 µM |

[a]Gelain (June 2006) 10th ISCPP, Strasbourg, France.

Desirably, ACAT1-selective inhibitors of the invention have an IC$_{50}$ value in the range of 1 nM to 100 µM. More desirably, ACAT1-selective inhibitors of the invention have an IC$_{50}$ value less than 100 µM, 50 µM, 10 µM, or 1 µM. Most desirably, ACAT1-selective inhibitors of the invention have an IC$_{50}$ value in the nM range (e.g., 1 to 999 nM).

In addition to the above-referenced ACAT1-selective inhibitors, it is contemplated that any conventional drug screening assay can be employed for identifying or selecting additional or more selective ACAT1 inhibitors or derivatives or analogs of known ACAT1 inhibitors. See, e.g., Lada, et al. (2004) J. Lipid Res. 45:378-386. Inhibitors of use in the invention can be derivatives of known ACAT inhibitors, which are selective for ACAT1 or can be identified and obtained from libraries of compounds containing pure agents or collections of agent mixtures.

Known ACAT inhibitors include derivatives of anilidic, ureidic or diphenyl imidazole compounds.

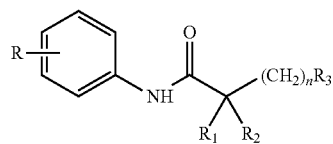

Anilidic Inhibitors

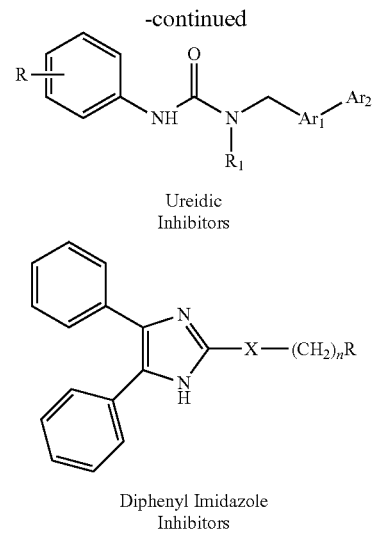

Ureidic Inhibitors

Diphenyl Imidazole Inhibitors

Examples of pure agents for library screens include, but are not limited to, proteins, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. In the case of agent mixtures, one may not only identify those crude mixtures that possess the desired activity, but also monitor purification of the active component from the mixture for characterization and development as a therapeutic drug. In particular, the mixture so identified may be sequentially fractionated by methods commonly known to those skilled in the art which may include, but are not limited to, precipitation, centrifugation, filtration, ultrafiltration, selective digestion, extraction, chromatography, electrophoresis or complex formation. Each resulting subfraction may be assayed for the desired activity using the original assay until a pure, biologically active agent is obtained.

Library screening can be performed in any format that allows rapid preparation and processing of multiple reactions such as in, for example, multi-well plates of the 96-well variety. Stock solutions of the agents as well as assay components are prepared manually and all subsequent pipetting, diluting, mixing, washing, incubating, sample readout and data collecting is done using commercially available robotic pipetting equipment, automated work stations, and analytical instruments for detecting the signal generated by the assay. Examples of such detectors include, but are not limited to, luminometers, spectrophotometers, calorimeters, and fluorimeters, and devices that measure the decay of radioisotopes. It is contemplated that any suitable ACAT enzymatic assay can be used in such screening assays. Moreover, preclinical efficacy of ACAT1 inhibitors can be assessed using conventional animal models of AD.

As disclosed herein, there are a number of suitable molecules that selectively inhibit the activity of ACAT1 without modulating the expression of ACAT1. Accordingly, in one embodiment of the present invention, a "selective inhibitor of ACAT1" or "ACAT1-selective inhibitor" specifically excludes molecules such as small inhibitory RNA (siRNA), antisense molecules, or ribozymes. However, in alternative embodiments, the ACAT1 selective inhibitor is a molecule, which selectively inhibits the expression of ACAT1, without modulating the expression of ACAT2. In so far as some RNAi molecules have been shown to induce significant neurotoxicity in brain tissue (McBride, et al. (2008) *Proc. Natl. Acad. Sci. USA* 105:5868-5873), specific embodiments of this invention embrace one or more siRNA or artificial microRNA molecules as the ACAT1-selective inhibitor. As is conventional in the art, siRNA or artificial microRNA refer to 19-25 nucleotide non-coding RNAs derived from endogenous genes that act as post-transcriptional regulators of gene expression. They are processed from longer (ca 70-80 nucleotide) hairpin-like precursors termed pre-miRNAs by the RNAse III enzyme Dicer. MicroRNAs assemble in ribonucleoprotein complexes termed miRNPs and recognize their target sites by antisense complementarity thereby mediating down-regulation of their target genes. By way of illustration, target sequences for siRNA or artificial microRNA molecules against mouse ACAT1 gene include, but are not limited to, those listed in Table 3 as SEQ ID NOs:37-40. SiRNA or artificial microRNAs against human ACAT1 gene (e.g., GENBANK Accession No. NM_000019, incorporated by reference) were also generated and shown to decrease human ACAT1 protein expression by 80% in human cells. Exemplary microRNA sequences targeting human ACAT1 include, but are not limited, those listed in Table 5 In a similar manner, Artificial microRNA against the ACAT1 gene in primates (e.g., GENBANK Accession No. XM_508738, incorporated by reference) can be developed, and used to selectively inhibit the expression of primate ACAT1.

Artificial microRNA or siRNA molecules which selectively inhibit the expression of ACAT1 can be administered as naked molecules or via vectors (e.g., a plasmid or viral vector such as an adenoviral, lentiviral, retroviral, adeno-associated viral vector or the like) harboring nucleic acids encoding the microRNA. Desirably, a vector used in accordance with the invention provides all the necessary control sequences to facilitate expression of the microRNA. Such expression control sequences can include but are not limited to promoter sequences, enhancer sequences, etc. Such expression control sequences, vectors and the like are well-known and routinely employed by those skilled in the art.

As indicated, selective inhibitors of ACAT1 find application in methods for stimulating the clearance of misfolded peptides or proteins generally from microglia and/or neurons, and decreasing the pathological changes associated with accumulation of these aberrant peptides and proteins, accumulation that results in neurodegeneration and the onset of diseases that would include but not be limited to AD, tauopathy, Parkinson's disease fronto-temporal dementia, Huntington Disease, and ALS. In a specific embodiment, the protein cleared from microglia is Aβ, which results in a decrease in the cognitive decline associated with amyloid pathology, and is a treatment for AD. In another embodiment, the protein cleared from neurons is tau, which results in a decrease in the cognitive decline associated with amyloid pathology, and is a treatment for AD. Generally, such methods involve administering to a subject in need of treatment an ACAT1-selective inhibitor in an amount that effectively reduces the activity of ACAT1 by at least 60%, 70%, 80%, 90%, 95%, 99% or 100%. Subjects benefiting from treatment with an agent of the invention include subjects confirmed as having a neurodegenerative disease such as AD, subjects suspected of having a neurodegenerative disease, or subjects at predisposed to have a neurodegenerative disease (e.g., subjects with a family history or Down syndrome and the risk of AD). In the context of this invention, a subject can be any mammal including human, companion animals (e.g., dogs or cats), livestock (e.g., cows, sheep, pigs, or horses), or zoological animals (e.g., monkeys). In particular embodiments, the subject is a human.

While certain embodiments of this invention embrace in vivo applications, in vitro use of agents of the invention are also contemplated for examining the effects of ACAT1 inhibition on particular cells, tissues or regions of the brain. In addition to treatment, agents of the invention also find application in monitoring the phenotypic consequences (e.g., rate of plaque formation or rate of cognitive decline) of amyloid pathology in rodent models of AD.

When used in therapeutic applications to treat AD, an ACAT1-selective inhibitor of the invention will have the therapeutic benefit of stimulating the clearance of amyloid beta from microglia and/or decreasing tau in neurons in the subject, decreasing or slowing the cognitive decline associated with amyloid pathology and/or tauopathy in the subject, and/or treating AD in the subject as compared to subjects not receiving treatment with the ACAT1-selective inhibitor. An ACAT1-selective inhibitor of the invention is expected to decrease or slow the cognitive decline associated by amyloid pathology and/or by tauopathy by 10%, 20%, 30%, 40%, 50%, 60% or more as compared to an untreated subject (e.g., as determined by Blessed Information-Memory-Concentration Test, the Blessed Orientation-Memory-Concentration Test, and the Short Test of Mental Status, or the Mini-Mental State Examination). Cognitive assessment can include monitoring of learning and retaining new information (e.g., does the subject have trouble remembering recent conversations, events, appointments; or frequently misplace objects), monitoring handling of complex tasks (e.g., can the subject follow a complex train of thought, perform tasks that require many steps such as balancing a checkbook or cooking a meal), monitoring reasoning ability (e.g., is the subject able to respond with a reasonable plan to problems at work or home, such as knowing what to do if the bathroom flooded), monitoring subject's spatial ability and orientation (e.g., can the subject drive, organize objects around the house, or find his or her way around familiar places), and/or monitoring language (e.g., does the subject have difficulty finding words to express what he or she wants to say and with following conversations). Based upon a decrease in signs and symptoms of AD, it is expected that AD in a subject receiving treatment will be prevented or slowed thereby treating the AD.

In treatment of other neurodegenerative diseases, such as tauopathy, Parkinson's disease, fronto-temporal dementia, Huntington Disease, and ALS, an ACAT1-selective inhibitor of the invention will have the therapeutic benefit of stimulating the clearance of misfolded proteins and peptides that have been linked to disease pathology, decreasing or slowing the pathological changes associated with the presence of the misfolded proteins and peptides in the subject, and/or treating the neurodegenerative disease in the subject as compared to subjects not receiving treatment with the ACAT1-selective inhibitor. An ACAT1-selective inhibitor of the invention is expected to decrease or slow the neurological changes associated with the specific disease pathology by 10%, 20%, 30%, 40%, 50%, 60% or more as compared to an untreated subject. Based upon a decrease in signs and symptoms of the neurodegenerative disease being treated, it is expected that further disease in a subject receiving treatment will be prevented or slowed thereby treating the neurodegenerative disease.

Successful clinical use of an ACAT1-selective inhibitor can be determined by the skilled clinician or veterinarian based upon routine clinical practice, e.g., by monitoring cognitive decline via methods disclose herein, functional activities (e.g., the Functional Activities Questionnaire), and sensory impairment and physical disability according to methods known in the art.

For therapeutic use, ACAT1-selective inhibitors can be formulated with a pharmaceutically acceptable carrier at an appropriate dose. Such pharmaceutical compositions can be prepared by methods and contain carriers which are well-known in the art. A generally recognized compendium of such methods and ingredients is. Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject agent from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Compositions of the present invention can be administered parenterally (for example, by intravenous, intraperitoneal, subcutaneous or intramuscular injection), topically, orally, intranasally, intravaginally, or rectally according to standard medical practices. Alternatively, the composition can be administered directly to the brain of the subject by a shunt or a catheter.

In certain embodiments of the present invention, the ACAT1-selective inhibitor is selectively delivered to the brain. For the purposes of the present invention, "selective delivery to the brain" or "selectively delivered to the brain" is intended to mean that the agent is administered directly to the brain of the subject (e.g., by a shunt or catheter; see, e.g., U.S. Patent Application No. 20080051691), to the perispinal space of the subject without direct intrathecal injection (see, e.g., U.S. Pat. No. 7,214,658), or in a form which facilitates delivery across the blood brain barrier thereby reducing potential side effects associated with ACAT1 inhibition in other organs or tissues. In this regard, formulation of the agent into a nanoparticle made by polymerization of a monomer (e.g., a methylmethacrylate, polylactic acid, polylactic acid-polyglycolic acid-copolymer, or polyglutaraldehyde) in the presence of a stabilizer allows passage of the blood brain barrier without affecting other organs with the agent. See, e.g., U.S. Pat. No. 7,402,573, incorporated herein by reference in its entirety. Furthermore, an exemplary system for selectively delivering microRNAs to the brain is the Adeno-Associated Virus (AAV) vector system. See, e.g., Cearley & Wolfe (2007) *J. Neurosc.* 27(37):9928-9940.

It has been shown that exosomes (i.e., natural transport nanovesicles in the range of 40-100 nm), which express Lamp2b fused to the neuron-specific rabies viral glycoprotein (RVG) peptide (YTIWMPENPRPGTPCDIFTNSRG-KRASNG; SEQ ID NO:45), can deliver siRNA specifically to neurons, microglia and oligodendrocytes in the brain, thereby resulting in specific gene knockdown (Alvarez-Erviti, et al. (2011) *Nature Biotechnol.* 29:341-345). Accordingly, in one embodiment of the present invention, the ACAT1-selective inhibitor is delivered to the brain via an exosome, in particular an exosome modified with a moiety that targets cells of the brain. Exosomes of use in this invention can be prepared by conventional methods, see, e.g., Sun, et al. (2010) *Mol. Ther.* 18:1606-1614. Likewise, therapeutic agents can be encapsulated within exosomes by conventional methods, e.g., incubating the therapeutic agent with an exosome preparation in saline at room temperature for several minutes, and separating the exosomes from unencapsulated drug and debris, e.g., by sucrose gradient separation. As described in the art, moieties that target cells of the brain include peptides that target cells of the brain (e.g., neurons, microglia and/or oligodendrocytes) as well as other targeting agents such as lipopolysaccharide, which has a high affinity for surface markers on microglia (Chow, et al. (1999) *J. Biol. Chem.* 274:10689-10692). Targeting peptides include, e.g., the RVG peptide (SEQ ID NO:45), which may be fused to membrane bound proteins, e.g., Lamp2b (Lysosome-associated membrane protein 2b) to facilitate integration into the exosome. Moreover, when the agent is a nucleic acid (e.g. siRNA or miRNA), the targeting peptide can be fused with a polyarginine peptide (e.g., nine D-arginines) so that the nucleic acid is electrostatically bound to the targeting moiety. In addition to using exosomes for delivery of the compositions, one of skill would understand that untargeted or brain-targeted liposome has been used successfully to facilitate delivery of the siRNA or small molecule inhibitors to brain tissue (Pardridge, W. M. 2007. *Adv. Drug Deliv. Rev.* 59:141-152; Pulford et al. 2010. *PLoS ONE* 5:e11085). As a result, Embodiments of the methods of the present invention include using of liposomes that are either targeted or untargeted.

In another embodiment of the invention, the ACAT1-selective inhibitor is delivered intranasally via an exosome, or a targeted liposome, or an untargeted liposome. Curcumin or Stat3 inhibitor, JSI-124 (cucurbitacin I), delivered via exosomes to the brain via the nasal route has been shown to accumulate in microglia and inhibit lipopolysaccharide (LPS)-induced microglial cell activation, delay experimental autoimmune encephalomyelitis (EAE) disease, and inhibit tumor growth in vivo (Zhuang, et al. (2011) *Mol. Ther.* 19:1769-1779). It is posited that transport occurs along the olfactory pathway and likely involves extracellular bulk flow along perineuronal and/or perivascular channels, which allows for delivering drugs directly to the brain parenchyma. Delivery along the extraneuronal pathway is likely not receptor-mediated and requires only minutes for a drug to reach the brain; whereas, delivery via an intraneuronal pathway along the primary olfactory sensory neurons involves axonal transport and requires several days for the drug to reach different areas of the brain. Therefore, in certain embodiments, the ACAT1-selective inhibitor of the invention is delivered to the brain, in particular microglia, by encapsulating within exosomes or liposome and intranasal administration.

The selected dosage level of an ACAT1-selective inhibitor will depend upon a variety of factors including the activity of the particular agent of the present invention employed, the route of administration, the time of administration, the rate of excretion or metabolism of the particular agent being employed, the duration of the treatment, other drugs, compounds and/or materials used in combination with the particular agent employed, the age, sex, weight, condition, general health and prior medical history of the patient being treated, and other factors well-known in the medical arts.

A physician or veterinarian having ordinary skill in the art can readily determine and prescribe the effective amount of the pharmaceutical composition required based upon the administration of similar compounds or experimental determination. For example, the physician or veterinarian could start doses of an agent at levels lower than that required in order to achieve the desired therapeutic effect and gradually increase the dosage until the desired effect is achieved. This is considered to be within the skill of the artisan and one can review the existing literature on a specific agent or similar agents to determine optimal dosing.

The invention is described in greater detail by the following non-limiting examples.

Example 1: Materials and Methods

Mice.

Mice were fed ad libitum with standard chow diet, maintained in a pathogen-free environment in single-ventilated cages and kept on a 12 hour light/dark schedule.

Generation of $Acat1^{-/-}$ Alz (A1$^-$/Alz) and $Acat2^{-/-}$ Alz (A2$^-$/Alz) Mice.

$Acat1^{-/-}$ and $Acat2^{-/-}$ mice (Meiner, et al. (1996) *Proc. Natl. Acad. Sci. USA* 93:14041-14; Buhman, et al. (2000) *Nat. Med.* 6:1341-1347) in C57BL/6 background are known in the art. The 3×Tg-Alz mice (Alzheimer's disease mice) in hybrid 129/C57BL/6 background contain two mutant human transgenes, hAPP harboring Swedish mutation (hAPPswe), and mutant htau (htau$_{P301L}$) under a neuron-specific promoter, and contain the knock-in mutant presenilin 1 (PS1$_{M146V}$) (Oddo, et al. (2003) *Neuron* 39:409-421). The CX3CR1/GFP$^{+/+}$ mouse has also been described (Jung et al. (2000) *Mol. Cell. Biol.* 10:4106-14).

Generation of $Acat1^{-M/-M}$ Mice.

Myeloid-specific knockout of ACAT1 ($Acat1^{-M/-M}$ mice) was achieved with the Cre-lox system in accordance with conventional methods. See, e.g., Cole, et al. (2012) *Mediat. Inflamm.* 2012:851798; Zhu, et al. (2008) *J. Biol. Chem.* 283:22930-41. Generally, mice with macrophage-specific deletion of Acat1 were generated by crossing Acat1 floxed ($Acat1^{flox/flox}$) mice with C57BL/6 mice expressing the Cre recombinase transgene under control of the lysozyme M promoter (B6.129-Lyzs$^{tm1(cre)Ifo}$/J, The Jackson Laboratory). Progeny from the cross that were heterozygous at the Acat1 locus and inherited the LysCre allele were identified by PCR (i.e., $Acat1^{+/-M}$). Intercrossing $Acat1^{+/-M}$ mice resulted in the production of the $Acat1^{+/+}$ (WT), $Acat1^{+/-M}$ (heterozygous), and $Acat1^{-M/-M}$ (homozygous) mice.

Antibodies.

Rabbit anti-ACAT1 (DM10) is known in the art (Chang, et al. (1995) *J. Biol. Chem.* 270:29532-29540). Mouse anti-human amyloid (6E10) and mouse anti-TUJ1 were from Covance (Dedham, Mass.). Rabbit anti-LAMP1 and mouse anti-p62/SQSTMI were from Abcam (Cambridge, Mass.). Mouse anti-EEAI was from BD Biosciences (Franklin Lakes, N.J.). Rabbit anti-CatB, mouse anti-tau antibody (Tau-5) and rabbit anti-Atg5 were from Millipore (Billerica, Mass.). Mouse anti-tubulin was from GenScript (Piscataway, N.J.). Rabbit anti-LC3 and rabbit anti-TFEB were from Novus (Littleton, Colo.). Rabbit anti-LC3, rabbit-anti mTOR, rabbit anti-phospho-mTOR (Ser2448), rabbit anti-p70S6K, rabbit anti-phospho-p70S6K (Ser371), rabbit anti-phospho-p70S6K (Thr389), rabbit anti-4E-BP, and rabbit anti-phospho 4E-BP(Thr37/46) were from Cell Signaling Technology (Danvers, Mass.). Mouse anti-human tau antibody (HT7) and mouse anti-human PHF-tau antibody (AT8) were from Thermo Fisher Scientific (Waltham, Mass.). Goat anti-GFAP and goat anti-Iba1 were from Santa Cruz (Dallas, Tex.). Mouse anti-actin was from Sigma (St. Louis, Mo.).

Cell Culture.

N9 microglial cells were maintained in RPMI-1640 with 10% FBS at 37° C. with 5% CO$_2$ in a humidified incubator. Primary microglia were prepared from mixed glial cultures isolated from mouse brains at postnatal day 0-3 as described (Saura, et al. (2003) *Glia* 44:183-89), were approximately 98% pure and were maintained in DMEM/F-12 (50:50) at 37° C. Neurons and astrocytes with approximately 90% to 95% purity were isolated from neonatal mice as described (Brewer (1997) *J. Neurosci. Methods* 71:143-55; Fagan, et al. (1999) *J. Biol. Chem.* 274:30001-7).

The mouse neuroblastoma cell line N2a was cultured in DMEM/OPTI-MEM (50:50) with 10% fetal bovine serum (FBS) at 37° C. with 5% CO$_2$ in a humidified incubator. Primary cortical neurons were isolated from mouse brains at postnatal day 0-3 using procedure as described (Brewer (1997) *Neurosci. Methods* 71:143-55; Bryleva, et al. (2010) *Proc. Natl. Acad. Sci. USA* 107:3081-86). Cortical neurons were plated in 6-well plates at 350,000 cells/well and grown in 2 mL/well NEUROBASAL A (Life Technologies, Grand Island, N.Y.) with 1×B27 (Life Technologies, Grand Island, N.Y.), 0.5 mM L-glutamine, and 5 ng/mL fibroblast growth factor (Sigma, St. Louis, Mo.). Half of the medium was replaced with fresh medium once every 7 days. After 14-21 days in culture, cells were used for individual experiments as described.

Preparation of Oligomeric Aβ.

Oligomeric Aβ1-42 was prepared as described previously (Stine, et al. (2003) *J. Biol. Chem.* 278:11612-22) with minor modifications. For example, OPTI-MEM instead of F-12 was used to prepare the peptide solution. Conjugation of Aβ1-42 to Cy3 was performed as previously described (Jungbauer, et al. (2009) *J. Mol. Recognit.* 22:403-13) using Cy3 Mono-Reactive Dye Pack (GE Healthcare Life Sciences, Pittsburgh, Pa.) according to the manufacturer's protocol.

Mouse Tissue Isolation.

Animals were sacrificed by $CO_2$ asphyxiation. The brains, adrenals and livers were rapidly isolated. Mice brains were dissected into various regions on ice within 5 minutes and were either used fresh (for ACAT enzyme activity assay) or were rapidly frozen on dry ice for other usage.

Aβ Clearance in Microglia.

N9 cells or primary microglia were plated in 12-well plates at a density of 150,000 cells/well in appropriate medium. On the next day, cells were washed twice with PBS and then incubated with 0.5 μM of oligomeric Aβ1-42 in serum-free medium containing 10 μg/ml BSA at 37° C. for indicated time. At the end of each time point, the conditioned media were collected, centrifuged at 1,000×g for 10 minutes to remove cell debris, and concentrated by precipitation with trichloroacetic acid (20% final concentration). The resulting proteins were re-dissolved and separated on a 16% tricine gel (Schagger (2006) *Nat. Protoc.* 1:16-22). The oligomeric Aβ (mono-, di-, tri-, and tetra-mers were analyzed by western blot and quantified using Image J software. After media removal, cells were washed three times with PBS and lysed in 1% SDS with protease inhibitors, and were analyzed for Aβ1-42 levels by ELISA.

Pulse-Chase Assay to Monitor Aβ Degradation.

Primary microglia were grown overnight in 12-well plates at a density of 150,000 cells/well in microglia medium. Cells were washed twice with PBS and incubated with 0.5 μM oligomeric Aβ1-42 in serum-free DMEM/F-12 (50:50) medium containing 10 μg/ml BSA for 30 minutes. After washing three times with PBS, cells were incubated in DMEM/F-12 (50:50) at 37° C. Cells were pre-incubated with or without inhibitors as indicated for 90 minutes before exposure to oligomeric A. At the indicated time, cells were washed twice with PBS and lysed in 1% SDS with protease inhibitors, and analyzed for Aβ1-42 levels by ELISA.

Isolation of Microglia from Adult Mouse Brain.

Microglia cells were isolated from adult mouse brains using CD11b MicroBeads (Miltenyi Biotec, San Diego, Calif.) as described previously (Nikodemova & Watters (2012) *J. Neuroinflamm.* 9:147). The CX3CR1/GFP$^{+/+}$ mice were used to examine the purity of microglia; GFP expression within the central nervous system of this mouse line is almost exclusively in microglia (Jung et al. (2000) *Mol. Cell. Biol.* 10:4106-14).

Stereotaxic Injection of Aβ into Mouse Brain.

Brain surgery was performed according to established methods. Mice (7-8 weeks old) were anesthetized with Tribromoethanol (250 mg/kg, i.p.) and a stainless steel needle (30 GA, Hamilton, Reno, Nev.) was stereotaxically inserted into the dentate gyrus of the hippocampus using the following coordinates from bregma: −2.2 mm anterior, +1.4 mm lateral and 2.1 mm depth. One μl of oligomeric Aβ1-42 (0.22 μg/ml) was manually injected into the hippocampus at a rate of 0.5 μl/min. and the needle was left in place for an additional 2 minutes at the end of injection. Ketoprofen (5 mg/kg) was used for postoperative analgesia. At the indicated time point, mice were euthanized, and the hippocampi and other parts of the brains were isolated, immediately frozen in liquid nitrogen and stored at −80° C. until analysis.

ACAT Activity Assay, Immunoprecipitation (IP) and Immunoblot Analyses.

Freshly isolated tissue samples were homogenized on ice in 50 mM Tris, 1 mM EDTA, pH 7.8 and solubilized in detergent using 2.5% CHAPS and 1 M KCl. The homogenates were centrifuged at 100,000 g for 45 minutes. The supernatants were used for ACAT activity assay in mixed micelles, and for IP and immunoblot analyses (Chang, et al. (1998) *J. Biol. Chem.* 273:35132-35141; Chang, et al. (2000) *J. Biol. Chem.* 275:28083-28092).

RNA Isolation, RT-PCR, and Real-Time PCR.

Total RNA was isolated with TRIZOL reagent (Invitrogen), stored at −80° C., and used for RT-PCR experiments, using the protocol supplied by the manufacturer. Real-time PCR was performed using the DYNAMO HS SYBR Green qPCR kit (New England Biolabs). Relative quantification was determined by using the delta delta CT method (Pfaffl, et al. (2002) *Nucleic Acids Res.* 30:e36). Mouse ACAT1 and human APP primers were designed using Oligo 4.0 Primer Analysis Software. Mouse ACAT2, neurofilament 120-kD (NF120), GAPDH primers sequences are known in the art (Sakashita, et al. (2003) *Lab. Invest.* 83:1569-1581; Kuwahara, et al. (2000) *Biochem. Biophys. Res. Commun.* 268: 763-766; Pan, et al. (2007) *BMC Mol. Biol.* 8:22). Sequences of primers used herein are listed in Table 2.

TABLE 2

| Gene | Amplicon Size | Sense/Antisense (5'->3') | SEQ ID NO: |
|---|---|---|---|
| ACAT1 | 274 | AGCCCAGAAAAATTTCATGGACACATACAG | 1 |
|  |  | CCCTTGTTCTGGAGGTGCTCTCAGATCTTT | 2 |
| ACAT2 | 530 | TTTGCTCTATGCCTGCTTCA | 3 |
|  |  | CCATGAAGAGAAAGGTCCACA | 4 |
| GAPDH | 186 | ATGGTGAAGGTCGGTGTG | 5 |
|  |  | CATTCTCGGCCTTGACTG | 6 |
| NF120 | 382 | ACGGCGCTGAAGGAGATC | 7 |
|  |  | GTCCAGGGCCATCTTGAC | 8 |
| HUMAN APP | 260 | CCCACTGATGGTAATGCTGGC | 9 |
|  |  | GGAATCACAAAGTGGGGATGG | 10 |
| ABCA1 | 96 | GGTTTGGAGATGGTTATACAATAGTTGT | 11 |
|  |  | TTCCCGGAAACGCAAGTC | 12 |
| ABCG1 | 85 | AGGTCTCAGCCTTCTAAAGTTCCTC | 13 |
|  |  | TCTCTCGAAGTGAATGAAATTTATCG | 14 |
| ABCG4 | 541 | CTGTCCTATTCCGTGCGGGA | 15 |
|  |  | GGGACTTCATGAGGGACACCACTT | 16 |
| APOE | 130 | AGCCAATAGTGGAAGACATGCA | 17 |
|  |  | GCAGGACAGGAGAAGGATACTCAT | 18 |
| CYP46A1 | 266 | CAGTGAAGGTCATGCTGGAG | 19 |
|  |  | CGCAATGAAGAAGGTGACAA | 20 |
| HMGR | 69 | TCTGGCAGTCAGTGGGAACTATT | 21 |
|  |  | CCTCGTCCTTCGATCCAATTT | 22 |
| HMGS | 77 | GCCGTCAACTGGGTCAA | 23 |
|  |  | GCATATATAGCAATGTCTCCTGCA | 24 |

TABLE 2-continued

| Gene | Amplicon Size | Sense/Antisense (5'->3') | SEQ ID NO: |
|---|---|---|---|
| HPRT | 91 | TTGCTCGAGATGTCATGAAGGA | 25 |
| | | AGCAGGTCAGCAAAGAACTTATAGC | 26 |
| LDLR | 68 | CTGTGGGCTCCATAGGCTATCT | 27 |
| | | GCGGTCCAGGGTCATCTTC | 28 |
| LRP | 95 | TGGGTCTCCCGAAATCTGTT | 29 |
| | | ACCACCGCATTCTTGAAGGA | 30 |
| SREBP1 | 121 | AACCAGAAGCTCAAGCAGGA | 31 |
| | | TCATGCCCTCCATAGACACA | 32 |
| SREBP2 | 150 | GTGGAGCAGTCTCAACGTCA | 33 |
| | | TGGTAGGTCTCACCCAGGAG | 34 |
| SQS | 137 | CCAACTCAATGGGTCTGTTCCT | 35 |
| | | TGGCTTAGCAAAGTCTTCCAACT | 36 |

The PCR reaction conditions for amplification of ACAT1, ACAT2, GAPDH, NF120 and Human APP included an initial denaturation at 94° C. for 5 minutes. Subsequently, 40 cycles of amplification were performed which included: denaturation at 94° C. for 10 seconds, annealing at 56° C. for 20 seconds, and elongation at 72° C. for 29 seconds. Amplification conditions for the remaining primers listed in Table 2 were as previously described (Van Eck, et al. (2003) *J. Biol. Chem.* 278:23699-23705).

In Situ Hybridization, Immunohistochemical and Thioflavin S Staining.

In situ hybridization was performed using standard procedures (Poirier, et al. (2008) *J. Biol. Chem.* 283:2363-2372) Immunohistochemistry was performed according to standard methods (Oddo, et al. (2003) supra). Thioflavin S staining was according to the protocol as described (Guntern, et al. (1992) *Experientia* 48:8-10), using free-floating sections. Confocal analysis of thioflavin S-positive amyloid deposits was performed using known methods (Dickson & Vickers (2001) *Neuroscience* 105:99-107).

Preparation of Formic Acid Brain Extracts.

Brain extracts were prepared as described (Kawarabayashi, et al. (2001) *J. Neurosci.* 21:372-81). Briefly, frozen tissue was suspended in 2% SDS with 1% protein inhibitor cocktail (Sigma, St. Louis, Mo.) and 1 mM PMSF (Sigma, St. Louis, Mo.). Brains were homogenized at 4° C. in the Bullet Blender (Next Advance, Averill Park, N.Y.) with stainless steel beads. Homogenates were centrifuged at 100,000×g for 1 hour at 4° C. and the supernatants (detergent-soluble fraction) were stored at −20° C. Pellets were re-suspended in 70% formic acid (FA) in water, homogenized in the Bullet Blender and centrifuged as described above. The supernatants (FA fraction) were stored at −20° C. Detergent soluble fractions and FA fractions were analyzed using ELISA. FA fractions were neutralized by 1:20 dilution into 1 M Tris phosphate buffer (pH 11) before ELISA.

Preparation of Brain Homogenates and Immunoblot Analysis of APP and its Fragments, and Human Tau.

(TY—Brain homogenates were prepared in the sucrose buffer with protease inhibitors at 4° C. according to published protocol (Schmidt, et al. (2005) *Methods Mol. Biol.* 299:267-278). Aliquots of homogenates were quickly frozen on dry ice and stored at −80° C. Upon usage, frozen homogenates were thawed on ice and centrifuged for 1 hour at 100,000 g at 4° C.; the supernatants contained soluble proteins including sAPPα and sAPPβ, while the pellet contained membrane-associated, insoluble proteins including full-length APP, CTFα, CTFβ, etc. Immunoblot analysis of APP and its fragments was according to (Cheng, et al. (2007) *J. Biol. Chem.* 282:23818-23828). The following antibodies were used: anti-human-Aβ 6E10 (1:5000) (Covance), anti-human-APP 369 antiserum (1:1000), anti-human-tau HT7 (1:1000) (Pierce), anti-human-tau phosphorylated at Ser202 AT8 (1:1000) (Pierce), monoclonal anti-HMG-CoA reductase IgG-A9 (1:3) (obtained from ATCC), and β-actin (1:5000) (Sigma). Densitometric analysis was performed using NIH Image software.

Aβ Analysis by ELISA.

Samples were prepared according to a standard protocol (Schmidt, et al. (2005) *Methods Mol. Biol.* 299:279-297), loaded undiluted or diluted 5-10 fold onto the "human β amyloid (1-40)" or "human β Amyloid (1-42)" ELISA plate (Wako), and analyzed according to protocol provided by Wako.

Contextual Fear Conditioning.

Contextual fear conditioning was performed according to a published protocol (Comery, et al. (2005) *J. Neurosci.* 25:8898-8902; Jacobsen, et al. (2006) *Proc. Natl. Acad. Sci. USA* 103:5161-5166). The auditory cue was from e2s (London, U.K.). GoldWave software program was used to edit the auditory cue; Winamp software was used to play the cue sound using the speakers. The digital sound level meter (RadioShack) was used to adjust the cue sound level to 87 dB. Each mouse behavior was recorded using a computer webcam (QuickCam from Logitech) and ANY-maze recording software. The videos were analyzed for freezing behavior, using time sampling at 5 second intervals.

Sterol Composition Analysis in Mice Brains.

Mice forebrains were homogenized and extracted using chloroform:methanol (2:1) (at 12 ml final vol. per mouse brain), dried down under nitrogen, and redissolved in MeOH. Ten percent of the sample was placed in a 2 ml GC/MS autosampler vial, dried down, and trimethyl-silyl derivatized overnight at room temperature with 0.5 ml TRI-SIL TBT (Pierce). One microliter of derivatized sample (or 0.1 µl for cholesterol measurements) was injected into a Shimadzu OP 2010 GC-Mass instrument. GC/MS analysis of sterols was according to known methods (Ebner, et al. (2006) *Endocrinology* 147:179-190) with modifications, using selected ion monitoring (cholesterol: 24 329, 353, 368, 458; desmosterol: 441, lanosterol: 393; 24S-hydroxycholesterol: 413) and standard curves for quantification.

Sterol, Fatty Acid and Cholesterol Ester Synthesis in Mice Brains.

Sterol and fatty acid synthesis in mice brains was measured according to known methods (Reid, et al. (2008) *J. Neurosci. Methods* 168:15-25). A similar method was developed to measure cholesterol esterification from $^3$H-cholesterol in vivo: mice were anesthetized with ketamine xylazine (0.1 ml/30 g body weight), mounted onto the Kopf stereotaxic instrument. After sagittal skin incision, $^3$H cholesterol at 10 µCi/mouse prepared in 3 µl of 5 mM methyl beta-cyclodextrin in PBS was injected into the right lateral ventricle with a glass syringe in 2 minutes. Mice were kept in cages for 3 hours, then euthanized by $CO_2$ gas. The forebrains were removed; lipids were extracted and redissolved in MeOH as described earlier. Ten percent of the redissolved sample was analyzed by TLC, using plates from Analtech, using solvent system hexanes:ethyl ether (anhydrous):acetic acid (60:40:1). The cholesterol and $^3$H cholesterol ester (CE) bands were scraped off the TLC plate and counted. Percent cholesterol esterification was determined by dividing the CE count by the total $^3$H cholesterol count.

Sterol Synthesis and Cholesterol Esterification in Primary Neuronal Cell Culture.

Hippocampal neurons were isolated from A1+/Alz and A1−/Alz mice at postnatal day 5 according to standard protocols (Brewer (1997) *J. Neurosci. Methods* 71:143-155; Price & Brewer (2001) *In Protocols for Neural Cell Culture*. Fedoroff & Richardson, editors. Totowa, N.J.: Humana Press, Inc. 255-264). Cells were seeded in 6-well dishes in triplicates at 300,000 cells/well, and grown in 3 ml/well NEUROBASAL A medium with 1×B27, 0.5 mM L-Gln and 5 ng/ml FGF for 14 days. Half of the medium was replaced with 25 fresh media once every 7 days. Forty-eight hours after the second media replacement, 50 pCi of [$^3$H] sodium acetate (100 mCi/mmol) in PBS was added per well for 3 hours. Lipids in cells and in media were extracted, saponified, and analyzed by using the same TLC system described herein. To minimize sterol oxidation, samples were protected from light and heat during lipid extraction, and were analyzed without storage. To improve separation, after sample loading, the TLC plate was placed under vacuum for 30 minutes prior to chromatography. $^3$H-labeled sterol bands were identified based on iodine staining of unlabeled sterols added to samples prior to lipid extraction. Rf values: lanosterol, 0.5; cholesterol, 0.38; 24SOH: 0.2. The bands were scraped off and counted. For each labeled sterol, the counts present in cells and in media were added to calculate the synthesis rate for that sterol. Cholesterol esterification in intact cells was conducted according to established methods (Chang, et al. (1986) *Biochemistry* 25:1693-1699); the $^3$H-oleate pulse time was 3 hours.

Analysis of Human Tau Levels in N2a Cells.

Plasmid DNA encoding WT-tau (pRK5-EGFP-Tau) and P301L-tau (pRK5-EGFPTau P301L) (Hoover, et al. (2010) *Neuron* 68:1067-1081) were obtained from ADDGENE (Cambridge, Mass.). N2a cells were grown in 6-well plates to ~50% confluence and transfected with the plasmid as indicated by using LIPOFECTAMINE 3000 (Life Technologies, Grand Island, N.Y.). Twenty-four hours after transfection, cells were incubated for 24 hours with or without the small molecule ACAT1-specific inhibitor K604 at concentrations as indicated in fresh DMEM/OPTI-MEM (50:50) containing 10% FBS, in the presence or absence of 5 mM 3-methyladenine (3MA) (Sigma, St. Louis, Mo.). K604 was stored as a 5 mM stock in ethanol at −20° C. until used. Cells were then lysed in RIPA buffer (50 mM Tris-HCl, pH 7.6, 1% TRITON X, 1% SDS, 0.5% sodium deoxycholate) with protease and phosphatase inhibitor cocktails (Sigma, St. Louis, Mo.), and analyzed for tau levels by western blot.

Gene KD by Transfection of siRNAs.

N2a cells were grown in 6-well plates to ~50% confluency and transfected with 10 nM of the siRNAs as indicated (Ambion, SILENCER Select predesigned siRNA. Atg5: ID# s62452, Control: Negative control No. 1) using LIPOFECTAMINE RNAIMAX (Invitrogen, Carlsbad, Calif.). Twenty-four hours later, cells were trypsinized, reseeded on 6-well plates, and then incubated at 37° C. with 5% $CO_2$ in a humidified incubator for hours. Cells were then transfected with pRK5-EGFP-Tau P301L and analyzed for tau levels as described herein.

Immunofluorescence Microscopy to Visualize LC3 Puncta.

Cells were grown overnight on poly-D-lysine-coated glass coverslips in 6-well plates at a density of 150,000-300,000 cells/well. Cells were washed with PBS and fixed with 4% paraformaldehyde for 15 minutes at room temp. Afterward, cells were washed three times with PBS, incubated for 60 minutes at room temperature in blocking buffer (3% BSA and 0.3% TRITON in PBS) and incubated overnight at 4° C. with anti-LC3 antibody (Cell Signaling Technology, Danvers, Mass.) in blocking buffer. Cells were then washed three times with PBS and incubated with ALEXA Fluor dye-conjugated secondary antibodies for 1 hour at room temperature. Afterward, cells were washed three times with PBS, rinsed with double-distilled water and mounted on glass slides with a drop of PROLONG Gold Antifade Reagent (Invitrogen, Carlsbad, Calif.). Confocal images were obtained using a Zeiss LSM 510 confocal microscope with a 63× objective. Image analysis was performed using Image J software.

Analysis of Cellular Acidic Compartments by Flow Cytometry.

Primary cortical neurons were pretreated for the time as indicated with 0.5 µM K604. The control cells received solvent vehicle only. Cells were then incubated with 50 nM LYSOTRACKER (Invitrogen, Carlsbad, Calif.) for 30 minutes and washed twice with PBS. LYSOTRACKER positive (cellular acidic) compartments were analyzed by using flow cytometry using a BD FACSCANTO (BD Biosciences, Franklin Lakes, N.J.). Dead cells were excluded from analyses by propidium iodide staining. Data were analyzed by using FlowJo software (Tree Star Inc, Ashland, Oreg.).

Bielschowsky Silver Staining.

Hemibrains were immersion fixed for 48 hours in 4% paraformaldehyde at 4° C. and sectioned at 50 µm using a vibrotome. The sections were mounted on slides and silver-stained according to Bielschowsky's method (Lewis, et al. (2000) *Nat. Genet.* 25:402-5; Liu, et al. (2012) *PLoS One* 7:e31302).

Statistical Analysis.

Statistical comparisons were made by using a two-tailed, unpaired Student's-test. The difference between two sets of values was considered significant when the P value was less than 0.05. Symbols used: *$p<0.05$; $p<0.01$; *$p<0.001$.

Example 2: ACAT Expression in Mouse Brains

Whether the brain has ACAT enzyme activity has not been previously shown. Therefore, to examine this, brain homogenates were prepared from wild-type, Acat1$^{-/-}$ (A1$^-$) and Acat2$^{-/-}$ (A2$^-$) mice. This analysis indicated that wild-type and A2$^-$ mouse brains contained comparable ACAT enzyme activity, while A1$^-$ mice brains contained negligible activity. Various brain regions prepared from wild-type mice all contained ACAT activities, while those from A1$^-$ mice brain contained no activity. Mouse ACAT1 is a 46-kDa protein (Meiner, et al. (1997) *J. Lipid Res.* 38:1928-1933). Immunoblot analysis showed that in homogenates prepared from mouse brain (but not from other mouse tissues), a non-ACAT1 protein band appeared in the 46-kDa region; the presence of this non-specific band precluded the use of immunoblotting or histochemical staining to identify ACAT1 in the mouse brain. To unambiguously identify ACAT1 protein, immunoprecipitation (IP) experiments were performed using detergent solubilized wild-type mouse brain extracts. The results of the IP experiment showed that ACAT activity could be efficiently immunodepleted by ACAT1-specific antibodies, but not by control antibodies. Immunoblot analysis of the immunoprecipates was then performed. The results showed that in homogenates from wild-type mouse brain regions, the ACAT1 antibodies specifically identified a 46-kDa-protein band; control experiments showed that this band was absent in homogenates prepared from the adrenals and brains of A1-mice. This result indicated that mouse brains express ACAT1 as the major ACAT isoenzyme.

To determine the ACAT1 mRNA distribution in mouse brains, in situ hybridization experiments were performed. Both hippocampus and cortex contain ACAT1 mRNA; with hippocampus showing a stronger signal. Other ACAT1 positive regions included choroids plexus, medial habenular nucleus, amygdala, and rostral extension of the olfactory peduncle. Subsequently, hippocampus-rich regions and cortex-rich regions were isolated from wild-type mice and their ACAT1 mRNA levels were compared by real-time PCR. The result validated the in situ hybridization experiment, and showed that ACAT1 mRNA was ~2-fold higher in hippocampus than in cortex. A separate, RT-PCR experiment using ACAT2-specific primers showed that only the thalamus-rich region, but no other brain regions, expressed low but detectable ACAT2 mRNA. It has similarly been shown that monkey brains have nearly undetectable levels of ACAT2 mRNA (Anderson, et al. (1998) *J. Biol. Chem.* 273:26747-26754).

Example 3: ACAT1-Deficient Alzheimer's Mice

While non-selective ACAT inhibition has suggested a role for ACAT activity in Alzheimer's pathology, it had not been shown whether the effects of the ACAT inhibitor acted by inhibiting ACAT activity and/or other biological process(es) in the mice brains. Accordingly, a genetic approach was employed to definitively assess the role of each isoenzyme in the pathology of Alzheimer's Disease. To carry out this analysis, a triple transgenic Alzheimer's mouse model (3×Tg-Alz; Oddo, et al. (2003) supra), which has been shown to be an effective research tool for studying Alzheimer's disease (Morrissette, et al. (2009) *J. Biol. Chem.* 284: 6033-6037) was crossed to an ACAT1 (A1$^-$) or ACAT2 (A2$^-$) knock-out mouse (Buhman, et al. (2000) *Biochim. Biophys. Acta* 1529:142-154) and amyloid pathology development was monitored in the Alzheimer's (Alz) mice with or without ACAT. The results showed that, at 4 month of age, when compared to the control Alz mice, the intraneuronal amyloid-β load in the hypocampal neurons was significantly decreased in the A1$^-$/Alz mice, but not in the A2$^-$/Alz mice. At 17 months of age, when compared to the control Alzheimer's mice, the sizes and densities of the amyloid plaques were significantly decreased in the A1$^-$/Alz mice. Behavioral analysis showed that ACAT1 deficiency rescued the cognitive decline manifested in the Alz mice. These results showed that ACAT1 gene inactivation caused a significant decrease in amyloid pathology in a mouse model for Alzheimer's Disease. Thus, ACAT1, but not ACAT2, is a therapeutic target for treating Alzheimer's Disease.

Example 4: Effect of A1$^-$ on Aβ Deposition/hAPPswe Processing, and on hTau

To investigate the effect of inactivating ACAT1 on amyloid and tau pathologies in the 3×Tg-Alz mice, A1$^-$/Alz mice were examined used the human specific anti-Aβ antibody 6E10 to perform intraneuronal immunostaining in the CA1 region of hippocampi of 4-month-old mice. Results showed that the staining was significantly diminished (by ~78%) in the A1$^-$/Alz mice. An enzyme-linked immunosorbent assay (ELISA) was next used to measure the total Aβ40 and Aβ42 levels in mouse brain homogenates at 17 months of age. Results showed that the Aβ42 levels were significantly decreased (by ~78%) in A1$^-$/Alz mice; the Aβ40 levels were also decreased, but the difference observed was not statistically significant. Control experiments showed that the brains of nontransgenic mice did not contain measurable Aβ. Thioflavin S was subsequently used to stain amyloid plaques in Alz mouse brains at 17 months of age. The results showed that in A1$^-$/Alz mice the amyloid plaque load in the hippocampi was significantly reduced (by ~77%); in the cortex, the amyloid plaque load in these mice showed a trend toward decreasing (p=0.17).

The effect of A1$^-$ on human APP processing in 4-month-old Alz mice was also analyzed. The human-specific anti-Aβ antibody 6E10 was used to detect full-length human APPswe (hAPP), and its proteolytic fragments sAPPα (hsAPPα) (soluble APP fragment produced by a secretase cleavage) and CTFβ (hCTFβ) (C-terminal APP fragment produced by β secretase cleavage) (Thinakaran & Koo (2008) supra). The results showed that in A1$^-$/Alz mice, hsAPPα and hCTFβ levels were decreased (by ~67% and by ~37%, respectively). Unexpectedly, the hAPP level was also significantly reduced (by ~62%). In contrast to the hAPP protein levels, there was no difference in hAPP mRNA levels between the A1$^+$/Alz mice and the A1$^-$/Alz mice. hAPP is synthesized in the endoplasmic reticulum in its immature form (with a molecular weight of ~105-kDa); the immature form moves from the endoplasmic reticulum to the Golgi via the secretory pathway (Cai, et al. (2003) *J. Biol. Chem.* 278:3446-3454), and becomes highly glycosylated (mature form has a molecular weight of ~115-kDa) (Weidemann, et al. (1989) *Cell* 57:115-126; Oltersdorf, et al. (1990) *J. Biol. Chem.* 265:4492-4497; Thinakaran, et al. (1996) *J. Biol. Chem.* 271:9390-9397). Thus, the effects of A1$^-$ on the immature and the mature forms of hAPP in young Alz mice (of 25-day old) were examined. The results showed that A1$^-$ decreased both forms to approximately the same extent (by ~52-54%), indicating that the effect(s) of A1$^-$ occur before newly synthesized hAPP exits the endoplasmic reticulum.

The Alz mice express both hAPP and endogenous (mouse) APP. It is possible that A1$^-$ may affect both the hAPP and the mAPP levels. To investigate the total APP levels in Alz mice, a different antibody (antiserum 369) was used, which recognizes the C-terminal fragments of both hAPP and mAPP (Buxbaum, et al. (1990) *Proc. Natl. Acad. Sci. USA* 87:6003-6006). The results showed that there was no detectable difference in the total APP levels between the non-Tg, the A1$^+$/Alz, and the A1$^-$/Alz mice, indicating that in the Alz mice strain, the hAPP is not overexpressed, when compared to the endogenous mAPP protein level. mAPP processing was also examined in mice that did not contain the hAPP gene. In these mice, A1$^-$ also did not affect the levels of mAPP (and its homolog APLP2 (Slunt, et al. (1994) *J. Biol. Chem.* 269:2637-2644)), or any of the proteolytic fragments derived from mAPP. These results led to the conclusion that A1$^-$ only reduced the hAPP level, and not the mAPP level. It is known that subtle sequence differences exist between hAPP and mAPP, and these differences may play an important role in causing differential fates of hAPP and mAPP (Du, et al. (2007) *J. Pharmacol. Exp. Ther.* 320:1144-1152; Muhammad, et al. (2008) *Proc. Natl. Acad. Sci. USA* 105:7327-7332). The results herein are in contrast to previous reports that indicated that an ACAT inhibitor affected the proteolytic processing of mouse APP, in addition to affecting the processing of hAPP (Hutter-Paier et al. (2004) supra). The discrepancy between the results herein and those of Hutter-Paier, et al. may be attributable to off-target or side effect(s) of the ACAT inhibitor used in their study.

Tau pathology is one of the hallmarks of Alzheimer's disease. Accordingly, the effect of A1− on mutant human tau (htau) was analyzed in 3×Tg-Alz mice. The results showed that at 4 months of age, A1− mice exhibited a significant decrease in htau (by ~57%), but in old mice at 17 months of age, A1− did not decrease the level of hyperphosphorylated htau. No significant change was observed in the number of hippocampal neurofibrillary tangles between the A1+/Alz and the A1−/Alz mice. These results indicated that A1− reduces mutant human tau content at young age, but does not attenuate tau pathology in Alz mice with old age.

Example 5: Effect of A1− on Cognitive Deficits of Alz Mice

To determine cognitive deficits of Alz mice, contextual (hippocampus dependent) and cued (amygdala dependent) memory tests were performed on age-matched (2, 9 and 12 months old) A1+/Alz, A1−/Alz and Non-Tg mice. The results showed that mice of all three genotypes at different ages were able to learn equally well. In contextual memory testing, there was no difference among these mice at 2 months of age; at 9 and 12 months, when compared to Non-Tg mice, the A1+/Alz mice exhibited a ~50% deficit, while the A1−/Alz mice exhibited no deficit. In cued memory tests, there was no difference among the mice at 2 months; at 9 months, when compared to Non-Tg mice, the A1+/Alz mice exhibited a trend toward a decline; however, the difference was not statistically significant. At 12 months, a statistically significant memory decline in the A1+/Alz mice was observed. In contrast, the A1−/Alz mice exhibited no deficit at either 9 or 12 months age. These results indicate that A1− ameliorated the hippocampal- and amygdala-dependent cognitive deficits in Alz mice at 9-12 months of age. As a control, contextual and cued tests were also performed on A1+ and A1− mice in the C57BL/6 background at 9 and 12 months of age. The results showed that the A1+ and the A1− mice were able to learn equally well; in either contextual or cued memory tests, wherein the difference between the A1− mice and the A1+ mice was not statistically significant.

Example 6: Effects of A1− on Sterol Metabolism in Alz Mouse Brains

ACAT is an important enzyme in cellular cholesterol homeostasis. It was contemplated that A1− may decrease hAPP content by affecting sterol metabolism in Alz mice brains. To demonstrate this, sterol fractions from A1+/Alz and A1−/Alz mouse brains were isolated and analyzed by GC/MS. The results showed that at 4 months of age, A1 deficiency caused a ~13% decrease in cholesterol content ($p=0.04$) and a ~32% increase in 24SOH content ($p=0.007$), without causing significant changes in either lanosterol or desmosterol content. A similar decrease in cholesterol content of the A1−/Alz mouse brains was observed when a colorimetric enzyme assay kit (Wako) as used to determine free cholesterol. It was also found that in the brains of 2-month-old Alz mice, A1 deficiency caused a ~10% decrease in cholesterol content and a ~23% increase in 24SOH content. Subsequently, the relative sterol synthesis and fatty acid synthesis rates were compared in the brains of these mice in vivo. The results showed that A1− caused a ~28% decrease in the sterol synthesis rate ($p=0.04$) without significantly changing the fatty acid synthesis rate. In mouse brains, cholesteryl ester contents are reported to be very low (Yusuf & Mozaffar (1979) *J. Neurochem.* 32:273-275; Liu, et al. (2009) *Proc. Natl. Acad. Sci. USA* 106:2377-2382). An attempt was made to measure CE in A1+ mice brains by separating the CE fraction from the free cholesterol fraction using column chromatography and determine the cholesterol content in CE by GC/MS after CE was saponified. While the low level of CE prevented a reliable measurement, the results suggested that CE might be present at no more than 1% of the total cholesterol mass in mice brains. Using a similar procedure to determine the 24SOH ester content, it was estimated that no more than 1% of total 24SOH was esterified in the brain. These results are consistent with the finding that ACAT prefers to use cholesterol to various oxysterols as its enzymatic substrate (Zhang, et al. (2003) *J. Biol. Chem.* 278:11642-11647; Liu, et al. (2005) *Biochem. J.* 391:389-397).

To demonstrate the functionality of ACAT1 in the intact mouse brain, a procedure was developed to measure CE synthesis in vivo by injecting $^3$H-labeled cholesterol (as a cyclodextrin complex) into intact mouse brains. The $^3$H-CE produced in A1+ and A1− mice was monitored 3 hours after injection. The result of this experiment showed that in A1+/Alz mice, a small percentage of $^3$H-cholesterol was converted to $^3$H-CE (0.56% in 3 hours); in contrast, such conversion was not detectable in the A1−/Alz mouse brains. This result demonstrated that ACAT1 in intact mouse brains can synthesize CE, although at a low rate.

The data herein indicated that in Alz mouse brains, A1− leads to an increased 24SOH level, which in turn leads to a down-regulation of the sterol synthesis rate. Studies in cell culture have suggested that 24SOH may down-regulate sterol synthesis by two mechanisms, namely by blocking transcriptional activations of SREBP2 target genes, and/or increasing the degradation rate of HMGR protein (Goldstein, et al. (2006) *Cell* 124:35-46). To test the first possibility, the mRNA levels of various SREBP2 and LXR target genes (i.e., HMGR, HMGS, SQS, LRP, LDLR, SREBP2, SREBP1, APOE, ABCA1, ABCG1, ABCG4, and CYP46A1) were compared in the A1+/Alz and the A1−/Alz mouse brains. This analysis indicated no significant alterations in the expression levels of these genes in the brains of mice with or without A1. To test the second possibility, immunoblot analysis was performed on brain homogenates prepared from the Alz mice with or without A1. The result showed that the HMGR protein content was decreased by ~65% in A1−/Alz mouse brains ($p=0.0009$), while the HMGR mRNA in A1− mice brains was not changed. Additional results showed that in Alz mice at 25-days of age, A1− caused a ~62% decrease in HMGR protein content, demonstrating that the effect of A1− on HMGR content occurs in mice at a young age.

Example 7: Biosynthesis of 24SOH in Hippocampal Neuronal Cell Cultures

The results described herein show that A1−/Alz mouse brains exhibit elevated 24SOH levels, indicating that in mouse neurons, A1− may cause an increase in the biosynthesis of 24SOH. In so far as cultured neurons isolated from brains have been shown to synthesize and secrete 24SOH (Russell, et al. (2009) supra; Kim, et al. (2007) *J. Biol. Chem.* 282:2851-2861), a hippocampal neuronal cell culture system was established from A1+/Alz and A1−/Alz mice to determine whether these cells exhibit an increase in the biosynthesis of 24SOH. CE biosynthesis was monitored in these neurons by incubation with labeled $^3$H-oleic acid. Upon entering cells, $^3$H-oleic acid is rapidly converted to $^3$H-CE by ACAT. Both the A1+ cells and the A1− cells synthesize CE; however, A1⁻ cells synthesize ³H-CE at a much reduced capacity compared to A1⁺ cells. The effect of A1⁻ on 24SOH biosynthesis was subsequent analyzed by feeding neurons with the sterol precursor ³H-acetate for 3 hours, then isolating and analyzing the labeled sterols present in the cells and media. The results showed that A1⁻ cells exhibited a reduced trend in cholesterol synthesis rate; the difference observed between A1⁺ cells and A1⁻ cells approached but did not reach statistical significance (p=0.05). The 24SOH synthesis rate in A1⁻ cells was significantly increased (by ~27%). The ³H-sterols in the media of A1⁺ and A1⁻ cells was also examined. The results showed that the ³H-cholesterol contents were not significantly different; in contrast, the ³H-24SOH content in A1⁻ cells was significantly (~56%) higher than that in A1⁺ cells. The percent of total ³H-sterols secreted into the media was calculated and it was found that neurons secreted only about 2% of total ³H-cholesterol, but secreted 13-15% of total ³H-24SOH into the media.

The results herein demonstrate that A1⁻ causes an increased 24SOH biosynthesis rate in neurons. Mouse neurons maintained in culture express CYP46A1 as a single 53-kDa-protein, which can be identified by immunoblot analysis (Russell, et al. (2009) supra). It is possible that the increased synthesis of 24SOH observed in A1⁻ neurons may be due to an increase in CYP46A1 protein content in these neurons. To determine this, CYP46A1 protein content in A1⁺ and A1⁻ neurons was analyzed by immunoblot analysis. The results showed that the intensities of the 53-kDa-protein band were comparable between the A1⁺/Alz and A1⁻/Alz cell types. This result indicates that in hippocampal neurons, the mechanism(s) involved in A1⁻-dependent increase in 24SOH synthesis does not require an increase in CYP46A1 protein content.

Example 8: 24SOH Provided to Alz Mouse Neurons Decreases hAPP Protein Content The observations made in intact A1⁻/Alz mouse brains (i.e., an increase in 24SOH content and a decrease in hAPP content) indicated that 24SOH may decrease hAPP content in neurons. To test this, hippocampal neurons from A1⁺/Alz mice were treated with 24SOH, and the hAPP protein content and the HMGR protein content were monitored in parallel. It was found that 1 µM 24SOH rapidly decreased the protein content of both hAPP and HMGR (within 3 hours). A separate experiment showed that 1-5 µM 24SOH caused a rapid decline in hAPP protein content without affecting its mRNA level. This result indicates that accumulation of 24SOH in neurons may down-regulate hAPP protein content in vivo.

Not wishing to be bound by theory, the current findings link cellular cholesterol trafficking with ACAT1, CYP46A1, 24SOH synthesis, and HMGR at the endoplasmic reticulum. In neurons, cholesterol trafficking in and out of the endoplasmic reticulum occurs. The unnecessary buildup of unesterified cholesterol at the endoplasmic reticulum (and other membranes) is toxic (Tabas (2002) *J. Clin. Invest.* 110:905-911; Warner, et al. (1995) *J. Biol. Chem.* 270:5772-5778). To minimize cholesterol accumulation, ACAT1, a resident enzyme located at the endoplasmic reticulum (Chang, et al. (2006) *Annu. Rev. Cell Dev. Biol.* 22:129-157), removes a portion of endoplasmic reticulum cholesterol by converting it to CE. ACAT1 deficiency leads to an increase in the endoplasmic reticulum cholesterol pool and raises the substrate level for CYP46A1, another endoplasmic reticulum resident enzyme (Russell, et al. (2009) supra). This leads to an increase in 24SOH biosynthesis in neurons. The increased 24SOH concentration leads to rapid down-regulation of hAPP protein content, limiting its capacity to produce Aβ. 24SOH secreted by neurons can enter astrocytes and other cell types and lead to efficient down-regulation of HMGR and cholesterol biosynthesis in these cells. Therefore, the beneficial effects of ACAT1 inhibition on cholesterol biosynthesis and on amyloid pathology is attributed to its ability to increase 24SOH level in Alz mouse brains. Therefore, agents that inhibit ACAT1 enzyme activity or decrease ACAT1 gene expression can ameliorate amyloid pathology, and have therapeutic value for treating Alzheimer's disease in humans. These results also indicate that agents that increase the concentration of 24SOH may help to combat Alzheimer's disease by decreasing APP content in the brain. Such agent include, but are not limited to, 24SOH itself.

Example 9: MicroRNA-Mediated Inhibition of ACAT1 Expression

Artificial microRNA molecules were designed to target the 5' end of the coding sequence of mouse ACAT1 sequences listed in Table 3.

TABLE 3

| micro RNA | ACAT1 Target Sequence | SEQ ID NO: |
|---|---|---|
| #52 | GGAGCTGAAGCCACTATTTAT | 37 |
| #53 | CTGTTTGAAGTGGACCACATCA | 38 |
| #54 | CCCGGTTCATTCTGATACTGGA | 39 |
| #55 | AACTACCCAAGGACTCCTACTGTA | 40 |

For example, the pre-microRNAs (including sense, antisense and loop regions) of microRNAs #54 and #55 were 5'-TGC TGT CCA GTA TCA GAA TGA ACC GGG TTT TGG CCA CTG ACT GAC CCG GTT CAC TGA TAC TGG A-3' (SEQ ID NO:41) and 5'-TGC TGT ACA GTA GGA GTC CTT GGG TAG TTT TGG CCA CTG ACT GAC TAC CCA AGC TCC TAC TGT A-3' (SEQ ID NO:42), respectively.

NIH-3T3 mouse fibroblasts were transiently transfected with one of several rAAV vectors encoding EmGFP and microRNA (miR) #52, #53, #54 or #55. Forty-eight hours post-transfection, GFP-positive cells were harvested by FACS. GFP-positive cells were washed then lysed in 10% SDS and syringe homogenized. Twenty microgram of protein per sample was subjected to SDS-PAGE. After western blot analysis, bands were quantified with ImageJ. ACAT1 intensity was normalized to GAPDH as a loading control and expressed as relative intensity. The results of this analysis are presented in Table 4.

TABLE 4

| Treatment | Relative Intensity |
|---|---|
| Mock Transfected | 1.00 |
| miR Negative Control | 1.02 |
| miR #52 | 0.77 |
| miR #53 | 0.56 |
| miR #54 | 0.54 |
| miR #55 | 0.39 |

This analysis indicated that microRNA molecules directed to mouse ACAT1 sequences could effectively decrease mouse ACAT1 gene expression by more than 50% compared to untreated controls.

Similarly, upon treatment of human HeLa cells or MCF-7 cells with either of the siRNAs listed in Table 5 (10 nM concentration for two days) decreased human ACAT1 protein expression by 80%.

TABLE 5

| siRNA Sequence (5'->3') | SEQ ID NO: |
|---|---|
| CAUGAUCUUCCAGAUUGGAGUUCUA | 43 |
| UAGAACUCCAAUCUGGAAGAUCAUG | 44 |

Example 10: Clinical Assessment of Therapeutic Efficacy in AD Patients

A cohort of subjects fulfilling NINCDS-ADRDA criteria (McKhann, et al. (1984) *Neurology* 34:939-44) for probable or possible AD will be recruited. The median age of the sample group will be determined. Clinical diagnosis will be made independently by, e.g., a psychiatrist and neurologist based on a checklist for symptoms of the disease with strict adherence to NINCDS-ADRDA criteria. Cognitive assessment will be recorded by trained clinical research nurses using the MMSE (Mini Mental State Examination; Folstein et al. (1975) *J. Psychiatric Res.* 12:189-98). Assessment will be followed a standardized protocol to maximize interrater reliability. All subjects will be followed up at yearly intervals, for a period of up to three years or more with repeat MMSE on each occasion.

During the trial period, subjects will either receive regular doses of an ACAT1-selective inhibitor or placebo. The rate of cognitive decline will be based on the average slope of MMSE points change per year. Differences in the average annual MMSE decline in the whole group by the presence or absence of the K variant of the ACAT1-selective inhibitor will be assessed by the Mann-Whitney U test. The subjects will then be grouped into four categories depending on their baseline MMSE scores (e.g., >24; ≤24 and >16; ≤16 and >8; ≤8 points). Differences in the average annual MMSE decline in the four categories by the presence or absence of the K variant of ACAT1-selective inhibitor will be initially assessed by independent t-tests. Linear regression analysis with the average annual MMSE decline as the dependent variable will then be used to assess for confounding and effect modification by the independent variables, e.g., MMSE at baseline, age, age of onset, and sex. It is expected that the results of this analysis will indicate that subjects receiving the ACAT1-selective inhibitor will exhibit a decrease in the rate or severity of cognitive decline as compared to subjects receiving placebo.

Example 11: Specificity of ACAT1 Inhibitors

It has been shown that when the ACAT inhibitor CP113818 or CI 1011 are administered to AD mice, amyloid plaques are significantly reduced and cognitive deficits are rescued, suggesting that inhibiting ACAT may prevent and/or slow down the progression of AD (Hutter-Paier, et al. (2004) supra; Huttunen & Kovacs (2008) supra; Huttunen, et al. (2009) supra). However, close comparison of the instant data and data of the prior art indicates that several important differences exist between the effects of the ACAT inhibitors and the effects of A1. CP113818 inhibits the processing of both human APP and mouse APP, whereas CI 1011 decreases the mature/immature ratio of hAPP. In contrast, A1⁻ only caused a decrease in the full-length human APP protein content and did not affect the mouse APP at any level or alter the mature/immature ratio of hAPP. Another important difference is that unlike the effect of CP113818, A1⁻ causes a reduction in the full-length hAPP content (Hutter-Paier, et al. (2004) supra). The differences in results indicate that the ACAT inhibitors used in the prior art are not selective for ACAT1.

ACAT is a member of the membrane bound O-acyltransferase (MBOAT) enzyme family (Hofmann (2000) *Trends Biochem. Sci.* 25:111-112), which includes sixteen enzymes with similar substrate specificity and similar catalytic mechanisms, but with diverse biological functions. In addition, many ACAT inhibitors are hydrophobic, membrane active molecules (Homan & Hamelehle (2001) *J. Pharm. Sci.* 90:1859-1867). When administrated to cells, it is likely that they partition into membranes at high concentration, thereby perturbing membrane properties nonspecifically. Although CP113818 and CI 1011 are designated as ACAT inhibitors, they also may inhibit other enzymes in the MBOAT family, and/or interfere with other biological processes.

The present data shows that inactivating the ACAT1 gene alone is sufficient to ameliorate amyloid pathology in the 3×Tg-AD mouse model. In this mouse model, A1⁻ acts to reduce Aβ load at least in part by reducing the hAPP protein content. In this context, the action of A1⁻ is similar to that of cerebrolysin, a peptide mixture with neurotrophic effects. It has been shown that cerebrolysin reduces Aβ in an AD mouse model, mainly by decreasing the hAPP protein content (Rockenstein, et al. (2006) *J. Neurosci. Res.* 83:1252-1261; Rockenstein, et al. (2007) *Acta Neuropathol.* 113:265-275). To further demonstrate that A1⁻ leads to hAPP content reduction, it was shown that the brains of A1⁻/Alz mice contain a significantly greater amount of 24SOH. Moreover, in neuron-rich cultures, it was shown that 24SOH, when added to the medium, leads to rapid decrease in hAPP protein content. It is possible that APP may act as a sterol sensing protein (Beel, et al. (2008) *Biochemistry* 47:9428-9446); sequence analysis shows that APP contains three CRAC motifs, a consensus motif known to bind cholesterol (Epand (2008) *Biochim. Biophys. Acta* 1778:1576-1582). It is also possible that cholesterol and/or oxysterol may directly interact with the hAPP protein to accelerate its rate of degradation. Alternatively, 24SOH may act indirectly by reducing membrane cholesterol content.

The data presented herein also show that in mouse brains, A1⁻ caused a decrease in HMGR protein and a decrease in cholesterol biosynthesis. This finding is consistent with previous analysis showing that inhibition of ACAT in macrophages or in CHO cells increases the ER "regulatory sterol pool" that causes down-regulation of HMGR levels and SREBP processing (Tabas, et al. (1986) *J. Biol. Chem.* 261:3147-3155; Scheek, et al. (1997) *Proc. Natl. Acad. Sci. USA* 94:11179-11183). Studies have suggested that the "regulatory sterol" could be cholesterol itself, and/or an oxysterol derived from cholesterol; however, whether oxysterol(s) plays important roles in regulating sterol biosynthesis in the brain in vivo has been debated (Bjorkhem (2009) *J. Lipid Res.* 50:S213-218). To address this issue, it has been shown that knocking out the 24-hydroxylase gene Cyp46a1 causes a near elimination in the 24SOH content, a decrease in cholesterol biosynthesis rate in the brain, and a decrease in cholesterol turnover in the brain; the total brain cholesterol content in the Cyp46a1$^{-/-}$ mice remained unchanged; Cyp46a1$^{-/-}$ did not affect the amyloid pathology in an AD mouse model (Lund, et al. (2003) *J. Biol. Chem.* 278:22980-22988; Kotti, et al. (2006) *Proc. Natl. Acad. Sci, USA* 103:3869-3874; Halford & Russell (2009) *Proc. Natl. Acad. Sci. USA* 106:3502-3506). In contrast, use of a cell-type non-specific promoter to drive the ectopic expression of Cyp46a1 in mouse brains shows that over-expressing Cyp46a1 causes a two-fold increase in 24SOH content and significantly ameliorates amyloid pathology in the AD mice (Hudry, et al. (2010) *Mol. Ther.* 18:44-53). In this study, a reduction in the hAPP protein content was not observed; instead, a decrease in hAPP processing, an increase in SREBP2 mRNA, and no change in brain cholesterol content was demonstrated. The present results show that in the A1$^-$/Alz mice, a 30% increase in 24SOH, a modest reduction in cholesterol biosynthesis rate, in brain cholesterol content, and a significant reduction in amyloid pathology occurred. The Cyp46a1 gene knockout or Cyp46a1 overexpression in mice may have produced compensatory effects that did not occur in the A1$^-$ mice, and vice versa; thus a direct comparison of the results described above is difficult. On the other hand, the combined results suggest that 24SOH may play an auxiliary but not an obligatory role in affecting cholesterol metabolism and amyloid biology, and its effects may be cell-type dependent. Based on other evidence, it has been independently proposed that a given oxysterol may play auxiliary but not obligatory roles in regulating cellular cholesterol homeostasis (Brown & Jessup (2009) *Mol. Aspects Med.* 30:111-122).

The instant data demonstrate a link between ACAT1, CYP46A1, 24SOH synthesis, and HMGR at the ER in cellular cholesterol trafficking. The unnecessary buildup of unesterified cholesterol at the ER (and other membranes) is toxic (Warner, et al. (1995) *J. Biol. Chem.* 270:5772-5778; Tabas (2002) *J. Clin, Invest.* 110:905-911). To minimize cholesterol accumulation, A1, a resident enzyme located at the ER (Sun, et al. (2003) *J. Biol. Chem.* 278:27688-27694), removes a portion of ER cholesterol by converting it to CE. A1$^-$ leads to an increase in the ER cholesterol pool and raises the substrate level for CYP46A1, another ER resident enzyme. This leads to an increase in 24SOH biosynthesis in neurons. The increased 24SOH and/or cholesterol concentration in the ER leads to rapid down-regulation of hAPP protein content, perhaps by accelerating its rate of degradation at the ER, thereby limiting its capacity to produce A. 24SOH secreted by neurons can enter astrocytes and other cell types, and lead to efficient down-regulation of HMGR and cholesterol biosynthesis in these cells. Therefore, the beneficial effects of A1$^-$ on cholesterol biosynthesis and on amyloid pathology in AD mouse brains is contributed to increase(s) in ER cholesterol and/or 24SOH level in the neurons. The instant data indicates that agents that selectively and specifically inhibit ACAT1 enzyme activity or decrease ACAT1 gene expression can ameliorate amyloid pathology, and have therapeutic value for treating AD in humans.

Example 12: Effect of Recombinant Adeno-Associated Virus Expressing Acat1 siRNA

Four different siRNA molecules (#52-#55; SEQ ID NOs: 37-40; Table 3) targeting the mouse Acat1 gene were inserted into an endogenous mouse microRNA (miR) scaffold using Invitrogen's RNAi design tool. The artificial miRNAs were ligated into the mammalian expression vector pcDNA6.2-GW/EmGFP-miR, These Acat1 miR constructs were tested along with a negative control (NC) miR (5'-TACTGCGCGTGGAGACG-3'; SEQ ID NO:46), which does not match the sequence of any known vertebrate gene, in NIH-3T3 mouse fibroblasts. The miRNAs were delivered to the cells using a standard cDNA transfection protocol. The results showed that Acat1 miRNAs #54 and #55 were effective in causing 50-60% reduction in the ACAT1 protein content in treated mouse 3T3 fibroblasts.

MicroRNAs #54 and #55, and the NC miR molecule were also subcloned into a rAAV backbone vector (AAV-6P-SEWB) that contained the neuron-specific hSyn promoter (Sibley, et al. (2012) *Nucl. Acids Res.* 40:9863-9875). This vector contained a strong nonspecific promoter that expressed Acat1 miRNAs in any cell type where the viral genome was expressed. For identification purposes, it also co-expressed GFP with the miRNAs. These three constructs were used to produce three recombinant AAV viruses. To test the efficacy and specificity of these viruses, cultured primary hippocampal neurons isolated from the triple transgenic Alzheimer neurons from AD mice (AD/Acat1$^{+/+}$ mice) were treated with the NC AAV, or with AAV that expressed miR containing siRNA Acat1 #55. Two weeks after viral infection, the effects of AAVs on cholesteryl ester biosynthesis were tested in neurons. The results showed that the AAV harboring siRNA Acat1 #55 reduced cholesteryl ester biosynthesis by more than 50% (P<0.01), when compared with values in NC virus treated cells.

The NC AAV or the Acat1 AAV (that included both siRNA Acat1 #54 and #55) were also injected into the hippocampal region of the AD mice at 4 months of age. After a single bilateral injection, mice were allowed to recover. One month after injection, mice were sacrificed and the ACAT1 enzyme activities in the mouse brain homogenates were analyzed using a standard ACAT enzyme activity assay in vitro. The result showed that when compared with the control values, the Acat1 AAV reduced ACAT1 enzyme activity by 42% (P<0.005).

Brain injections can cause various inflammatory responses in mice. Therefore, in a separate experiment, transcript levels of various inflammatory markers were assessed one month after brain injections. The results showed that the brain injections of PBS and/or AAV caused alterations in the transcript levels of various inflammatory markers (iba, GFAP, TNFα, and iNOS); however, the degree of alteration was modest (i.e., within 20% of control values).

Subsequently, single bilateral injections of PBS, or NC AAV or Acat1 AAV were made into the hippocampal region of AD mice with ACAT1 (AD/ACAT1$^{+/+}$), or AD mice without ACAT1 (AD/ACAT1$^{-/-}$); both mouse strains were at 10 months of age. After injections, mice were allowed to recover, and were sacrificed two months later (at 12 months of age) to determine Aβ1-42 content. The results showed that injecting AAV unexpectedly caused a small but significant reduction of Aβ1-42 levels in the AD mice. Nevertheless, additional results also showed that injecting the AAV that expressed the Acat1 KD microRNA caused a stronger and clear reduction in the Aβ1-42 level (FIG. 1).

In the AD mouse brain, Acat1 genetic ablation (Acat1$^{-/-}$) caused a 60-80% reduction in the Aβ1-42 content; however, residual Aβ1-42 was still present in the brains of the AD/Acat1$^{-/-}$ mouse brain. In a control experiment, it was shown that, in the AD/Acat1$^{-/-}$ mouse brain, treating with either Acat1 AAV or with NC AAV caused about a 25% reduction in the residual Aβ1-42 levels (FIG. 1), confirming that injecting AAV could cause a small but significant Aβ1-42 reduction, in a manner independent of its ability to recognize the Acat1 mRNA sequence.

Using the residual Aβ1-42 level remaining in the AD/Acat1$^{-/-}$ mouse brain injected with AAV as the baseline value, it was estimated that the efficiency of Acat1 AVV to reduce Aβ1-42 in an ACAT1 sequence-dependent manner was 70%.

Overall, these results showed that siRNAs against ACAT1 can be employed to cause inhibition of ACAT1 enzyme activity and to cause significant Aβ1-42 reduction in the AD mouse brains in vivo, after cognitive deficit occurred in these mice.

Example 13: Clearance of Oligomeric Amyloid Beta

Monomers of Aβ assemble to form oligomeric Aβ (oAβ). In Alzheimer's Disease, oAβ causes synaptic dysfunction and neurodegeneration. Strategies to reduce oAβ levels by decreasing Aβ production and/or by enhancing its clearance are promising therapies to treat AD. As demonstrated herein, gene knockout or gene knockdown of Acat1 in the triple transgenic (3×Tg-AD) mouse model reduces the levels of full-length human APP and Aβ42. Therefore, it was important to determine whether the inhibition of ACAT1 stimulates oAβ clearance in microglia, which are known to play an essential role in the proteolytic clearance of Aβ.

Figure 2:
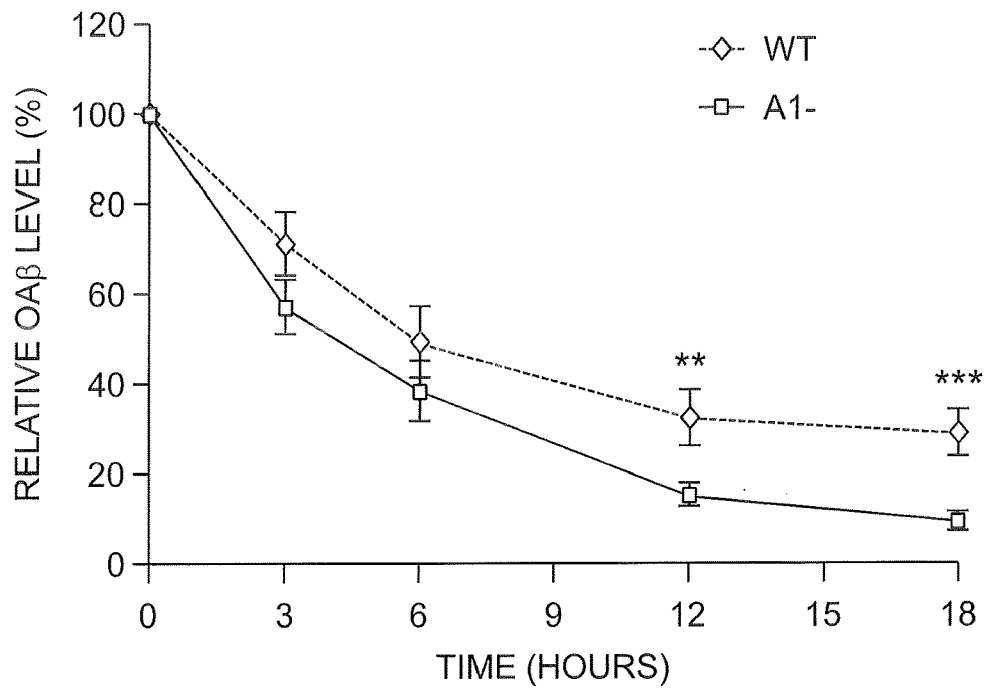
FIG. 2 shows that oligomeric Aβ (oAβ) degradation is increased in A1$^-$ microglia. Wild-type (WT) or A1$^-$ microglia were incubated with 0.5 μM oAβ in serum-free DMEM/F-12 (50:50) containing 10 μg/ml BSA for the indicated time. The remaining Aβ levels (1+2+3+4 mers) in the media were analyzed by western blot analysis. Bands were quantified with image J software. Residual oAβ levels at 0 hour were set as 100%. Quantification of results from 4 independent experiments is shown. Data are mean±SEM, p<0.01, *p<0.001.

Primary microglia from normal (WT) and Acat1$^-$ knock-out (A1$^-$) mouse brains were cultured in vitro. Oligomeric Aβ42 (0.5 μM) in serum-free DMEM/F-12 (50:50) medium containing 10 μg/ml BSA was added to the culture and the culture was incubated for 0, 3, 6, 12 or 18 hours. The remaining Aβ levels (1+2+3+4mers) in the media were analyzed by western blot analysis. Bands were quantified with image J software and the results of this analysis are presented in FIG. 2. This analysis indicated that oAβ degradation was increased in A1$^-$ microglia compared to wild-type.

Figure 3:
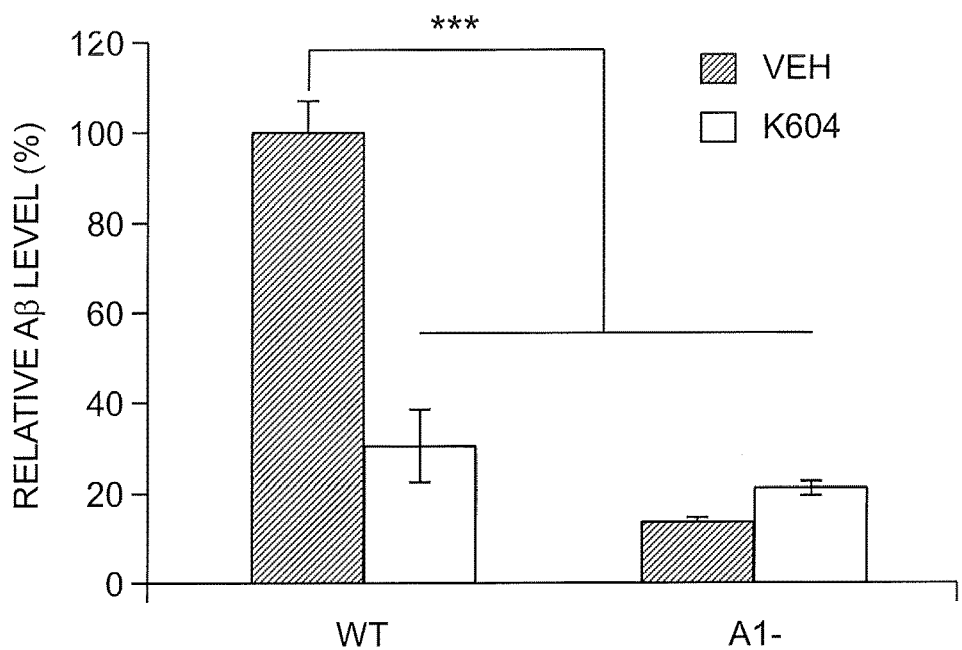
FIG. 3 shows that the ACAT1-selective inhibitor, K604, promotes oAβ degradation in microglia. WT or A1$^-$ microglia were treated with K604 at 1 μM in DMEM/F-12 (50:50) with 10% FBS for 24 hours. Control (Veh) or K604-treated microglia were subsequently incubated with 0.5 μM oAβ in serum-free DMEM/F-12 (50:50) containing 10 μg/ml BSA for 18 hours. At the end of incubation, the media were collected and the residual oAβ levels were detected by western blot analysis. Quantification was performed with image J software (mean±SEM, ***p<0.001).

Clearance of oAβ in WT microglia and WT microglia pretreated with the ACAT1-selective inhibitor K604 was also determined. The results of this analysis indicated that in microglia without ACAT1, i.e., WT microglia pre-treated with K604, the ability to clear oAβ42 from the medium was significantly enhanced (by up to 65%; FIG. 3).

Figure 4A:
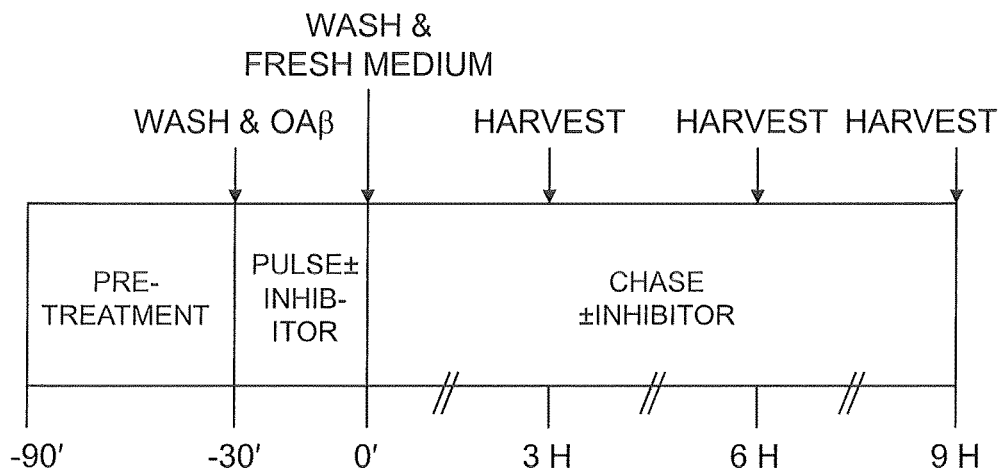
FIG. 4A shows a diagram of the procedure used to conduct pulse-chase experiments in the presence or absence of proteolytic inhibitors.
Figure 4B:
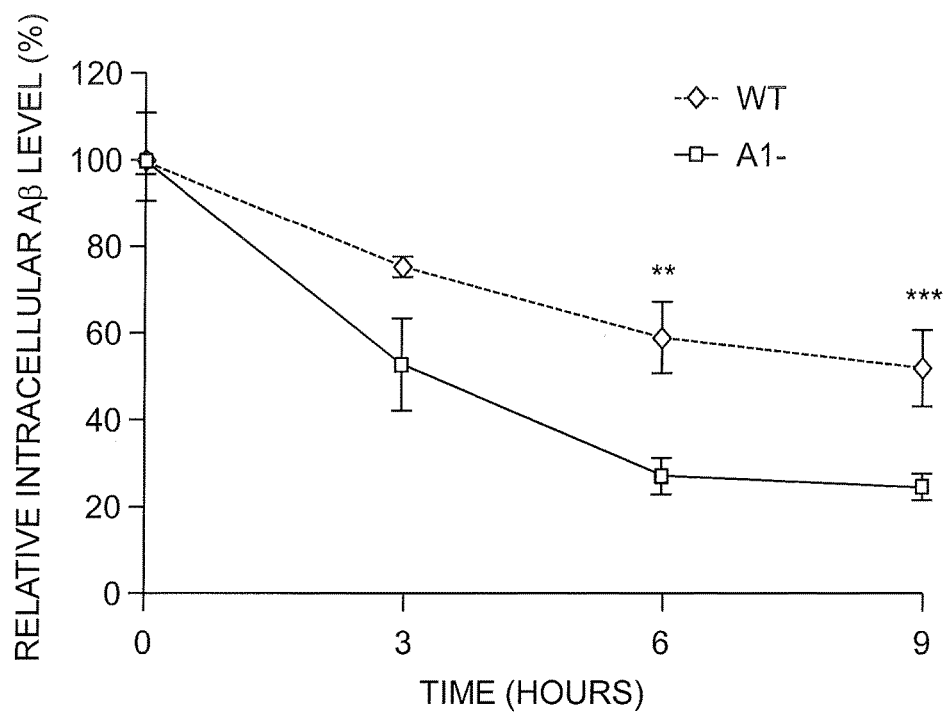
FIG. 4B shows that intracellular Aβ degradation is increased in A1$^-$ microglia. WT and A1$^-$ microglia were incubated with 0.5 μM oAβ for 30 minutes. Cells were washed with pre-warmed PBS (twice) and pre-warmed medium (once) and subsequently incubated in fresh serum-free DMEM/F-12 (50:50). At the end of incubation time indicated, cells were washed with PBS twice and lysed with 1% SDS containing protease inhibitor cocktail. Intracellular oAβ levels present in the lysates were examined by ELISA; the values were normalized by cellular protein contents. The data are averages of 3 independent experiments. (mean±SEM, p<0.01, *p<0.001)
Figure 4C:
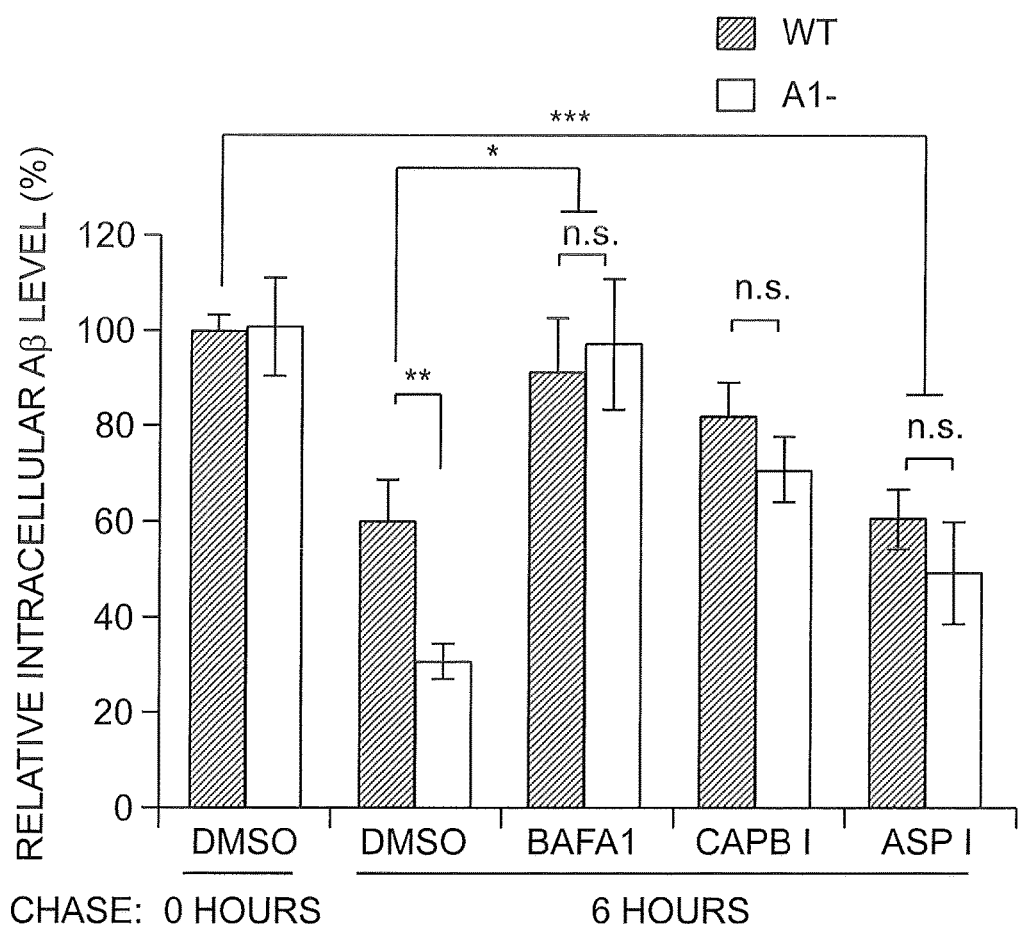
FIG. 4C shows that the increase in intracellular Aβ degradation observed in A1$^-$ microglia is abolished if cells are pretreated with specific lysosomal inhibitors. WT or A1$^-$ microglia were pretreated with DMSO only; with bafilomycin A1 (BafA1), a lysosomal v-ATPase inhibitor (250 nM); with Ac-LVK-CHO, a cell permeable cathepsin B inhibitor (CapB I) at 1 μM; or with pepstatin A methyl ester, a cell permeable aspartyl peptidase inhibitor at 25 μM, for 60 minutes. Cells with or without the inhibitors were further incubated with 0.5 μM oAβ for 30 minutes. Cells were washed with pre-warmed PBS (twice) and pre-warmed medium (once) and then further incubated in fresh serum-free DMEM/F-12 (50:50) for 6 hours. At the end of incubation, cells were washed with PBS twice and lysed with 1% SDS containing a protease inhibitor cocktail. Intracellular oAβ levels were examined by ELISA. The values were normalized by cellular protein contents. The data are averages of 3-4 independent experiments. (mean±SEM, n.s. not significant, *p<0.05, p<0.01, ***p<0.001).

Pulse-chase of oAβ42 was also carried out (FIG. 4A) and the fate of oAβ42 was monitored via an ELISA assay. This analysis indicated that intracellular oAβ42 degradation was significantly increased (by 50%) in A1$^-$ microglia (FIG. 4B). Interestingly, it was also found that A1$^-$ microglia express increased levels of cathepsin B, a key Aβ degrading enzyme located mainly in the lysosome. Differences in degradation of oAβ42 observed in the WT and A1$^-$ microglia was abolished by pre-incubation of these cells with a cell permeable cathepsin B inhibitor (Ac-LVK-CHO) (FIG. 4C). In light of these results, quantitative PCR (qPCR) analysis was performed it was found that the expression levels of several lysosome-specific genes, including Lamp1, Lamp2, Cathepsin B and Cathepsin D, were all significantly upregulated in A1$^-$ microglia, as well as in microglia freshly isolated from 3×Tg-AD/A1$^-$ mice (at 4 months and 12 months of age). Collectively, these data show that inhibition of ACAT1 in microglia activates lysosomal biogenesis to stimulate Aβ1-42 degradation, and implicates ACAT1 in microglia as a therapeutic target for treating AD.

Example 14: ACAT1 Inhibition in Microglia Stimulates Autophagy-Mediated Lysosomal Proteolysis and Increases Aβ1-42 Clearance Experiments were performed to examine the effect of inhibiting ACAT1 in microglia on autophagy-mediated proteolysis. Primary microglia were isolated from neonatal wild-type (WT) and Acat1-knockout (A1-KO) mice. Biochemical analysis showed that ACAT1 protein was absent and ACAT activity was dramatically reduced in microglia. WT or A1-KO microglia were incubated for up to 18 hours with human Aβ1-oligomers and Aβ1-42 levels present in the media were determined using western blot analysis. The results showed that after 12 and 18 hours, Aβ1-42 levels in A1-KO microglia-conditioned media were significantly lower (by 53% and by 68%, respectively).

It is known that microglia secrete certain proteolytic enzymes that can degrade Aβ in the extracellular milieu (Lee & Landreth (1996) *J. Neural Transm.* 117:949-960). To test whether A1-KO promotes the degradation of Aβ extracellularly, conditioned medium from WT or A1-KO microglia was collected and oligomeric Aβ1-42 was added in order to evaluate its degradation. Using western blot analysis, results showed that conditioned media isolated from WT and A1-KO microglia degraded oligomeric Aβ1-42 at comparable levels. Then, to determine if A1-KO microglia take up more Aβ1-42 than WT microglia, which could account for the increased Aβ1-42 clearance, Aβ internalization was monitored in microglia. First, Cy3-conjugated Aβ1-42 (Cy3-Aβ1-42) was prepared as previously described (Jungbauer, et al. (2009) supra). After conjugation, western blot analysis revealed that similar to the results obtained with unlabeled oligomeric Aβ1-42, Cy3-Aβ1-42 contained mainly Aβ1-42 monomers, trimers and tetramers. Next, WT or A1-KO microglia were incubated with Cy3-Aβ1-42 for 3 hours and uptake of Cy3-Aβ1-42 was monitored by flow cytometry. The results showed that intracellular Cy3-Aβ1-42 levels in A1-KO microglia were 22% higher than that found in WT microglia. To further confirm findings described above, WT and A1-KO microglia were incubated with unlabeled oligomeric Aβ1-42 for up to 18 hours. Subsequently, intracellular levels of Aβ1-42 were analyzed by ELISA. Increased intracellular levels of Aβ1-42 were detected in A1-KO microglia at 3, 6, and 12 hours after incubation with oligomeric Aβ1-42.

Scavenger receptors, including SR-A1 and CD36, are involved in binding and/or phagocytosis of Aβ in various cells in culture and in vivo (Frenkel, et al. (2013) *Nat. Commun.* 4; Paresce, et al. (1996) *Neuron* 17:553-565; Yamanaka, et al. (2012) *J. Neurosci.* 32:17321-17331; Yang, et al. (2011) *Neurobiol. Dis.* 42:221-230). To test whether scavenger receptors mediated uptake of Cy3-Aβ1-42 in this system, primary microglia were incubated with Cy3-Aβ1-42 in the presence of fucoidan, a broad-based inhibitor of several scavenger receptors (Paresce, et al. (1996) *Neuron* 17:553-565); uptake of Cy3-Aβ1-42 was monitored. Flow cytometry analysis showed that fucoidan significantly inhibited the uptake of Cy3-Aβ1-42 in primary microglia, and the amounts of Cy3-Aβ1-42 present in WT and A1-KO microglia were very similar in the fucoidan-treated cells. These results indicated that A1-KO is associated with an increase in scavenger receptor-mediated endocytosis of Aβ1-42 in microglia. Using quantitative PCR (qPCR), similar mRNA levels of SR-A1 or CD36 were detected in WT and A1-KO microglia.

Results showed that there were differences in intracellular Aβ1-42 levels in both WT and A1-KO microglia for the first 6 hours; levels increased and then gradually decreased. Then, 18 hours after incubation with oligomeric Aβ1-42, similar amounts of intracellular Aβ1-42 were present in WT and A1-KO microglia. This observation indicated that intracellular degradation of Aβ1-42 is increased in A1-KO microglia. To examine this, pulse-chase experiments were performed. Primary microglia were incubated with oligomeric Aβ1-42 for 30 minutes and then washed extensively to remove the remaining Aβ1-42 in the media. The results showed that WT and A1-KO microglia internalized comparable levels of Aβ1-42 in 30 minutes. After washing, the intracellular Aβ1-42 levels were measured at various chase times by ELISA. The results showed that after 6 and 9 hours chase time, levels of intracellular Aβ1-42 were approximately 50% lower in A1-KO microglia as compared to levels in WT microglia, indicating that A1-KO microglia have an increased capacity to degrade Aβ1-42 intracellularly. Considered together, these data demonstrated that A1-KO stimulated oligomeric Aβ1-42 clearance in microglia by increasing uptake of Aβ1-42, and by promoting intracellular degradation of Aβ1-42.

Experiments were then performed to determine whether A1-KO in microglia increases lysosome-specific gene expression and lysosome volume. Microglia take up fibrillar and oligomeric forms of Aβ, and degrade them within the late endosomes/lysosomes (LE/LS) (Jiang, et al. (2008) *Neuron* 58:681-693; Majumdar, et al. (2007) *Mol. Cell Biol. Cell* 18:1490-1496; Yang, et al. (2011) *Neurobiol. Dis.* 42:221-230). To monitor the fate of internalized Aβ1-42 in microglia, the cellular localization of Cy3-Aβ1-42 was examined using immunofluorescence microscopy. After incubating WT or A1-KO microglia with Cy3-Aβ1-42 for 3 hours, the LE/LS were visualized with anti-LAMP1 antibody; the early endosomes (EE) were visualized with anti-EEA1 antibody. Results showed that approximately 70% of internalized Cy3-Aβ1-42 co-localized with the LE/LS, while less than 20% of Cy3-Aβ1-42 co-localized with the EE. These data indicated that within this time period, internalized Cy3-Aβ1-42 is mainly transported to the LE/LS.

To determine whether A1-KO increases lysosomal degradation of Aβ1-42, pulse-chase experiments were again performed in the presence or absence of several inhibitors of lysosomal proteolysis. Bafilomycin A1 (BafA1) is a cell-permeable, specific inhibitor of vacuolar-type H (+)-ATPase; when added to cells, it inhibits acidification and protein degradation in lysosomes (Yoshimori, et al. (1991) *J. Biol. Chem.* 266:17707-17712). The results showed that in both WT and A1-KO microglia, Baf treatment almost completely blocked intracellular Aβ1-42 degradation. Cathepsin B (CatB) is a cysteine protease that degrades Aβ in vitro and in vivo (Mueller-Steiner, et al. (2006) *Neuron* 51:703-714; Sun, et al. (2008) *Neuron* 60:247-257). Cathepsin D (CatD) is an aspartate protease and degrades Aβ in vitro (Hamazaki (1996) *FEBS Lett.* 396:139-142). Cells were treated with a cell permeable CatB specific inhibitor (CatBi) or with pepstatin A methyl ester (PepA), a cell-permeable aspartate protease inhibitor, and then analyzed for intracellular Aβ1-42 degradation by performing the pulse-chase experiments described above. The results showed that CatBi significantly inhibited intracellular Aβ1-42 degradation, and intracellular levels of Aβ1-42 in WT and A1-KO microglia became comparable. In contrast, PepA treatment failed to inhibit intracellular Aβ1-42 degradation in WT microglia, and slightly inhibited Aβ1-42 degradation in A1-KO microglia. As a result, the intracellular Aβ1-42 levels became similar in WT and A1-KO microglia after PepA treatment. These results indicated that CatB activity in the lysosomes accounts for the increased intracellular Aβ1-42 degradation observed in A1-KO microglia. CatB is translated initially as a precursor form proCatB and is glycosylated in the Golgi apparatus. Glycosylated proCatB is then transported into the lysosomes and proteolytically cleaved by CatD to form mature CatB in the same compartments; the mature CatB becomes fully functional (Katunuma (2010) *J. Signal Transduct.* Article ID:375345). Protein expression levels of CatB in WT or A1-KO microglia were then determined and results showed that the protein levels of both mature CatB (30 kDa) and total CatB (pro- and mature CatB) were significantly increased in A1-KO microglia; the level of proCatB (40 kDa) in A1-KO microglia showed a trend toward increasing, but the difference did not reach statistical significance.

The transcription factor EB (TFEB) regulates lysosomal protein biogenesis by increasing transcription of target genes that belong to the Coordinated Lysosomal Expression and Regulation (CLEAR) network, including CatB (Sardiello, et al. (2009) *Science* 325:473-477). To test whether A1-KO up-regulates expression of CLEAR network genes in microglia, mRNA levels of various TFEB target genes were examined using qPCR analysis. The results showed that the expression levels of LAMP1, LAMP2, CatB, CatD and hexoaminidase A (HEXA) were all significantly increased in A1-KO microglia, indicating that A1-KO increased TFEB-mediated lysosomal protein biogenesis in microglia. To examine this interaction further, microglia cells were stained with LYSOTRACKER, a fluorescent dye that accumulates in acidic compartments (i.e., LE/LS), and then examined using flow cytometry. The results revealed that A1-KO microglia contained 21% more in LE/LS volume than WT microglia. Together these results demonstrate that A1-KO in microglia induces increased expression of lysosome-specific genes and also increases lysosome volume.

Next, the effect of ACAT1 inhibition on microglial function was investigated. Experiments were performed in an established microglial cell line (N9). Alterations in Aβ clearance and lysosome volume in N9 cells were monitored. The ACAT1-specific inhibitor, K604 was used. As expected, K604 efficiently blocked ACAT activity in a dose-dependent manner in N9 cells. Then, N9 cells were pre-treated with K604 for 24 hours, followed by incubation of the cells with oligomeric Aβ1-42 for 12 hours in the presence of K604. The residual oligomeric Aβ1-42 levels present in the media were analyzed by western blot. Results showed that K604 treatment lowered oligomeric Aβ1-42 levels by 58%. K604 treatment did not further reduce the residual cholesterol esterification activity present in the A1-KO microglia, nor did it further reduce the oligomeric Aβ1-42 levels in conditioned media recovered from the A1-KO microglia culture. This indicated that in N9 microglial cells, the effect of K604 on oligomeric Aβ1-42 clearance was a result of ACAT1 inhibition. Experiments were then performed to determine whether K604 promoted uptake of oligomeric Aβ1-42. N9 cells were pre-treated with K604 for 8 hours, followed by incubation with Cy3-Aβ1-42 for 3 hours in the presence of K604. Subsequent flow cytometry analysis demonstrated that K604 increased the uptake of Cy3-Aβ1-42 by 23%.

The effect of K604 treatment of N9 cells on expression of TFEB-target genes was also examined. After treatment of N9 cells with K604 (8 hours), qPCR analysis was performed. The results showed that in cells treated with K604, mRNA expression levels of five different TFEB-target genes were significantly increased. In addition, LYSOTRACKER staining followed by flow cytometry analysis revealed that K604 increased LE/LS volume by 27%. Interestingly, K604 at a concentration of 0.1 µM, inhibited ACAT activity by 80%, and still significantly enhanced LYSOTRACKER-fluorescence intensity in N9 cells. This result indicated that partial or incomplete blockage of ACAT1 activity in microglia is sufficient to increase TFEB-dependent lysosomal biogenesis. Considered together, these data were consistent with data showing that in A1-KO microglia, inhibiting ACAT1 activity with K604 promoted oligomeric Aβ1-42 clearance in N9 cells by stimulating Aβ1-42 uptake and increasing LE/LS volume.

The results described above demonstrated that inhibition of ACAT1 activity in microglia promoted lysosome biogenesis. It is known that autophagy is closely associated with lysosome biogenesis (Saftig & Klumperman (2009) *Nat. Rev. Mol. Cell Biol.* 10:623-635). As a result, experiments were performed to determine if inhibition of ACAT1 activity increases autophagy in microglial cells. The lipidated form of LC3 (LC3-II) (Kabeya, et al. (2000) *EMBO J.* 19:5720-5728) is a marker for autophagy (Mizushima & Yoshimori (2007) *Autophagy* 3:542-545). Using western blot techniques it was found that LC3-II levels were significantly higher in A1-KO microglia as compared to WT microglia. Further, N9 cells treated with K604 had even higher levels of LC3-II as compared to vehicle-treated cells. Since degradation of LC3-II affects its steady-state levels, autophagy flux was monitored using the lysosome inhibitors Baf and $NH_4Cl$, which inhibit lysosomal acidification and lead to LC3-II accumulation (Mizushima & Yoshimori (2007) *Autophagy* 3:542-545). Treating primary microglia with Baf, or treating N9 cells with $NH_4Cl$ further increased LC3-II levels in these cells, indicating that ACAT1 inhibition increased autophagy flux without interfering autophagosome clearance. It also was found that when used at a concentration as low as 0.1 µM, K604 treatment produced a significant increase in LC3-II levels in N9 cells, indicating that partial inhibition of ACAT1 activity is sufficient to promote autophagy. LC3 punctuate structure is a well-established method for estimating autophagosome formation in intact cells (Mizushima, et al. (2010) *Cell* 140: 313-326). Thus, LC3 puncta was quantified in microglia by fluorescence microscopy. Consistent with the results of the western blot analysis, A1-KO microglia were shown to contain 3.5 times more LC3 puncta than WT microglia. Similarly, the N9 cells treated with K604 contained 2.5 times more LC3 puncta than vehicle treated cells.

Mammalian target of rapamycin (mTOR) is a serine/threonine protein kinase that regulates cell growth, proliferation, motility, and survival (Laplante & Sabatini (2012) *Cell* 149:274-293). In various cell types, inhibition of mTOR by nutrient starvation or by treatment with various mTOR inhibitors increases both autophagy and lysosome biogenesis (Settembre, et al. (2012) *EMBO J.* 31:1095-1108; Zhou, et al. (2013) *Cell Res.* 23:508-523). To determine if the effects of ACAT1 inhibition on autophagy and lysosome biogenesis is dependent on inhibition of mTOR signaling, expression levels of mTOR and its kinase activity levels were examined using western blot techniques. Comparable levels of mTOR activity, revealed by measuring the phospho-p70S6K and phospho-4E-BP levels, were present in WT and A1-KO microglia. Additionally, when WT and A1-KO microglia were nutrient-starved by incubating in Hank's Balanced Salt Solution (HBSS) for 3 hours, or by treatment with a potent mTOR inhibitor, Torin1 (Guertin & Sabatini (2009) *Sci. Signal.* 2:e24) for 3 hours, mTOR activity was suppressed to similar levels in both cell types. Then, the effect of K604 treatment on mTOR signaling in N9 cells was examined using western blot techniques. The results showed that K604 treatment failed to decrease levels of phospho-p70S6K and phospho-4E-BP, whereas Torin1 treatment strongly reduced the levels of these proteins. These results demonstrated that the mechanism(s) by which ACAT1 inhibition leads to increases in autophagy and lysosome biogenesis is distinct from that of mTOR inhibition.

It also is known that autophagy can be activated by endoplasmic reticulum stress (Ogata, et al. (2006) *Mol. Cell. Biol.* 26:9220-31). Since ACAT1 is a resident enzyme in the endoplasmic reticulum (Chang, et al. (1995) *J. Biol. Chem.* 270:29532-29540), and over-accumulation of cholesterol and/or unesterified fatty acids in the endoplasmic reticulum can induce endoplasmic reticulum stress (Erbay, et al. (2009) *Nat. Med.* 15:1383-1391; Feng, et al. (2003) *Nat. Cell Biol.* 5:781-792), it was determined whether ACAT1 inhibition leads to over-accumulation of cholesterol in the endoplasmic reticulum, which in turn stimulates endoplasmic reticulum stress, leading to autophagy. Thus, experiments were performed to evaluate the effect of K604 on mRNA levels of several unfolded stress response (UPR) genes using qPCR. K604 treatment did not alter the expression levels of the UPR genes in N9 cells, and the mRNA expression levels of these UPR genes were similar in WT and A1-KO microglia. Splicing of XBP1 mRNA is an indicator for endoplasmic reticulum stress (Yoshida, et al. (2001) *Cell* 107:881-891). As a result, un-spliced and spliced forms of XBP1 were examined by RT-PCR; it was found that K604 treatment of N9 cells, or A1-KO in primary microglia, did not cause detectable splicing of XBP1 mRNA. Together, these results demonstrated that, under the conditions employed, ACAT1 inhibition did not cause endoplasmic reticulum stress in microglia.

Experiments were then performed to determine if ACAT1 inhibition and mTOR inhibition could produce additive effects on autophagic flux and lysosome volume. p62 is a selective autophagic substrate (Bjorkey, et al. (2005) *J. Cell Biol.* 171:603-614) and p62 protein levels inversely correlate with autophagic activity (Mizushima, et al. (2010) *Cell* 140:313-326). Autophagic flux in primary microglia was monitored by quantifying the LC3-II and p62 levels using western blot techniques. A three hour incubation in HBSS resulted in decreases in p62 and increases in LC3-II, with greater changes observed in A1-KO microglia than in WT microglia. LE/LS volume was examined in WT and A1-KO microglia with or without HBSS incubation. The results showed that the effects of A1-KO and HBSS treatment on lysosome volume were additive. Similarly, in N9 cells, the effects of K604 and Torin1 treatment on lysosome volume were additive. Together, these data indicated that the effects of ACAT1 and mTOR inhibition on autophagic flux and lysosome volume were additive.

Atg5 is an essential protein for autophagy (Mizushima, et al. (2001) *J. Cell Biol.* 152:657-668). To explore the relationship between augmented autophagy and lysosome biogenesis produced by ACAT1 inhibition, autophagosome formation in N9 cells was inhibited through siRNA knockdown (KD) targeting Atg5, followed by treatment of the KD cells with Torin1 or K604. Western blot analysis revealed that as compared to control KD cells, Atg5 protein levels were almost completely eliminated (reduced by approximately 95%). Unlike control KD cells, virtually no LC3-II was identified in Atg5 KD cells when they were treated with either K604 or Torin1. It also was found that Atg5 KD dramatically reduced LC3-positive puncta in K604-treated or Torin1-treated cells. These results demonstrated that the effect of K604 on autophagosome formation requires Atg5. Finally, the effect of K604 on lysosome biogenesis in N9 cells after Atg5 KD was determined. Results showed that in Atg5 KD cells, ACAT1 inhibition with K604 failed to increase LYSOTRACKER staining.

3-methyladenine (3MA) is a class III PI3-kinase inhibitor that is widely used as an autophagy inhibitor (Mizushima, et al. (2010) *Cell* 140:313-326). Experiments were performed that demonstrated that in cells treated with 3MA, ACAT1 inhibition with K604 failed to increase cellular acidic compartments in N9 cells. In contrast, control experiments showed that in Atg5 KD cells, Torin1 increased LYSOTRACKER staining to a level similar to levels in control KD cells. Experiments then were performed to determine mRNA expression levels of TFEB target genes; Atg5 KD abolished the effect of K604 on TFEB target gene expression, whereas Torin1 treatment was associated with increased expression of these genes in Atg5 KD cells. These data demonstrated that unlike Torin1, the effect of K604 (ACAT1 inhibition) on lysosome biogenesis depends on autophagosome formation in N9 cells. It also was found that in 3MA-treated N9 cells, ACAT1 inhibition with K604 failed to result in increased uptake of Cy3-Aβ1-42, indicating that ACAT1 inhibition-mediated enhancement of oligomeric Aβ1-42 uptake also involved autophagy.

Recent studies have shown that the transcription factor TFEB up-regulates autophagy and lysosomal protein biogenesis (Settembre, et al. (2011) *Science* 332:1429-1433; Settembre, et al. (2012) *EMBO J.* 31:1095-1108). To determine whether the effect of ACAT1 inhibition (use of K604) on autophagy and lysosome biogenesis depended on expression of TFEB, expression levels of TFEB genes were knocked down (TFEB KD) in N9 cells. The results showed that TFEB KD decreased TFEB expression in N9 cells by approximately 90%. In TFEB KD cells, treating cells with either K604 or with Torin1 still led to increases in LC3-II levels, indicating that augmenting autophagosome formation through treatment with either agent did not depend on TFEB expression. Then, the effect of ACAT1 inhibition (K604) or mTOR inhibition (Torin1) on lysosome biogenesis in TFEB KD cells was examined. Flow cytometric analysis revealed that in TFEB KD cells, K604 failed to increase LYSOTRACKER staining. In TFEB KD cells, Torin1 treatment still increased LYSOTRACKER staining, but the increase was significantly attenuated as compared to control KD cells. Finally, expression levels of TFEB-target genes in TFEB KD cells were examined using qPCR. Results showed that neither K604 nor Torin1 treatment led to up-regulation of TFEB-target gene mRNA levels. Considered together, these results demonstrated that both autophagosome formation and TFEB are required to mediate the effect of ACAT1 inhibition on lysosome biogenesis. However, TFEB is not required to mediate the effect of ACAT1 inhibition autophagosome formation.

In intact cells, ACAT1 activity is mainly controlled by the endoplasmic reticulum cholesterol pool (Chang, et al. (1997) *Annu. Rev. Biochem.* 66:613-638). Therefore, experiments were performed to determine if altering cellular cholesterol levels influenced the effect of ACAT1 inhibition on lysosome biogenesis. Cellular cholesterol was reduced by treating cells with a squalene synthase inhibitor CP-340868 (SSI), or with an HMG CoA reductase inhibitor lovastatin (statin). In cells treated with statin, mevalonate was provided in the growth medium such that the statin effect is mainly on cholesterol, but not on mevalonate derived non-sterol metabolites (Goldstein & Brown (1990) *Nature* 343:425-430). Conversely, cellular cholesterol was increased by loading cells with cholesterol in complex with methyl cyclodextrin, which is a soluble cholesterol carrier (cholesterol/MCO). After these treatments, cellular acidic compartments were quantified using LYSOTRACKER staining followed by flow cytometry. The results showed that inhibiting endogenous cholesterol biosynthesis by SSI eliminated the difference in LE/LS volume between WT and A1-KO microglia that had previously been identified. The effect of SSI, however, was negated when cells were also loaded with cholesterol in the growth medium. Similarly, in N9 cells treated with statin or with SSI, ACAT1 inhibition (K604 treatment) failed to increase cellular acidic compartments; the statin effect and the SSI effect were negated when cells were loaded exogenously with cholesterol. These data demonstrated that the effect of ACAT1 inhibition on LE/LS volume was sensitive to cellular cholesterol content. Additionally, statin treatment promoted LYSOTRACKER staining in N9 cells. Statins are known to inhibit Akt/mTOR signaling in addition to their cholesterol-lowering effects (Roudier, et al. (2006) *Mol. Cancer Ther.* 5:2706-2715). It also was found that statin treatment reduced phospho-p70S6K (Thr389) levels, indicating that statin can induce mTOR-dependent lysosome biogenesis by partially inhibiting mTOR kinase activity.

Experiments were then performed to determine whether blocking cholesterol biosynthesis influenced the effect of ACAT1 inhibition (K604 treatment) on autophagosome formation in N9 cells. Treatment of N9 cells with statin or SSI increased levels of LC3-II, similar to earlier results (Cheng, et al. (2006) *Annu. Rev. Cell Dev. Biol.* 22:129-157). It is known that cholesterol depletion reduces autophagosome/lysosome fusion in vitro (Koga, et al. (2010) *FASEB J.* 24:3052-3065). Thus, reducing cellular cholesterol levels by adding statin or SSI may inhibit fusion of autophagosome and lysosomes, leading to accumulation of LC3-II. ACAT1 inhibition in the cells (K604) in combination with statin or SSI treatment further increased LC3-II levels. However, in statin- or SSI-treated cells, p62 levels were unchanged. These data indicated that under cholesterol-lowering conditions, when ACAT1 activity was inhibited, increases in autophagosome accumulation still were observed, although there was no effect to increase autophagic flux. Additional results showed that in N9 cells treated with cholesterol-biosynthesis inhibitors, Torin1 also failed to reduce p62 levels. Considered together, these data demonstrated that the effect of ACAT1 inhibition on lysosome volume is sensitive to cholesterol content.

Experiments were then performed in vivo to determine if ACAT1 knockout affected lysosome biogenesis in microglia and to define the mechanism. Expression levels of TFEB-target genes were compared in microglia isolated from 3xTg-AD/ACAT1$^{+/+}$ (3xTg-AD/A1$^+$) and 3xTg-AD/Acat1$^{-/-}$ (3xTgAD/A1$^-$) mice. 3xTg-AD is an AD mouse model that displays memory dysfunction by 9 months of age and starts to develop significant Aβ1-42 accumulation at 10 months of age (Clinton, et al. (2007) *Neurobiol. Dis.* 28:76-82; Murphy, et al. (2013) *Mol. Ther.* 21:1497-1506; Oddo, et al. (2003) *Neuron* 39:409-421). Highly pure (93-95%) microglia populations were isolated from brains of these mice at 4 and months of age using anti-CD11b-coated magnetic beads. Using this method to isolate microglia results in microglia with in vivo characteristics, such as gene expression (Chiu, et al. (2013) *Cell Rep.* 4:385-401; Nikodemova & Watters (2012) *J. Neuroinflammation* 9:147). Using qPCR, results showed that expression levels of TFEB-target genes were all significantly higher in microglia from 3xTg-AD/A1$^-$ mice as compared to levels found in microglia from 3×Tg-AD/A+ mice. These data indicated that A1-KO increased lysosome biogenesis in microglia in adult AD mice in vivo, before and after the onset of the disease.

Experiments were subsequently performed to investigate whether A1-KO stimulated Aβ clearance in vivo. In addition to the WT mice and the global A1-KO mice, myeloid-specific ACAT1$^{-/-}$ (A1$^{-M/-M}$) mice were used. Biochemical analyses showed that, unlike A1-KO mice, A1$^{-M/-M}$ mice have ACAT1 deletion in microglia but not in neurons or astrocytes. Injections of Aβ to mouse brain areas such as the hippocampus have been used to reproduce pathological features of AD. For instance, intracerebroventricular injection of synthetic Aβ1-42 oligomers, but not Aβ1-42 fibrils, impairs long-term memory in mice (Balducci, et al. (2010) *Proc. Natl. Acad. Sci. USA* 107:2295-2300). Further, repeated injection of oligomeric Aβ1-42 into the hippocampus of awake mice leads to several neuropathological markers of AD, including memory dysfunction and neuronal loss (Brouillette, et al. (2012) *J. Neurosci.* 32:7852-7861) and most of the injected Aβ1-42 is cleared in 72 hours. It also has been reported that microglia are rapidly recruited to the site of microinjection (El Khoury, et al. (2007) *Nat. Med.* 13:432-438; Mandrekar, et al. (2009) *J. Neurosci.* 29:4252-4262). Using a similar approach, oligomeric Aβ1-42 was injected into the dentate gyrus of the hippocampal region in age matched WT, A1$^{-M/-M}$ and A1-KO mice, and clearance of Aβ1-42 was monitored in tissue by ELISA. Twenty-four hours after injection, more than 60% of oligomeric Aβ1-42 was cleared from the hippocampus, and residual Aβ1-42 levels were comparable in all three groups of mice. Seventy-two hours after injection, however, significantly less residual Aβ1-42 remained in brain tissue of A1$^{-M/-M}$ mice and A1-KO mice as compared to brain tissue of WT mice. These results were consistent with microglial promotion of Aβ1-42 clearance in vivo. Therefore, ACAT1 inhibition in vivo resulted in increased lysosome biogenesis and stimulation of Aβ clearance from microglia.

Example 15: ACAT1 Blockage Enhances Autophagy and Reduces Human P301L-tau Content at the Pre-Symptomatic Stage ACAT1 Blockage Promotes Autophagy in the Mouse Neuroblastoma Cell Line N2a. To investigate whether blocking ACAT1 increases autophagy in neuronal cells, we began our study by treating N2a cells with a potent ACAT1-specific inhibitor K604 (Ikenoya, et al. (2007) *Atherosclerosis* 191:290-297). The result showed that at 0.1 to 1 μM, K604 inhibited ACAT activity by 60-80%. Subsequently, K604 was added to N2a cells at concentrations from 0.1 to 1 μM for 24 hours, and LC3 levels were examined by western blot. The result showed that K604 increased the LC3-II/LC3-I ratio, a reliable marker for autophagosome formation (Mizushima, et al. (2010) *Cell* 140:313-326), in a dose-dependent manner. In mammalian cells, autophagy can be activated by inhibition of mTOR (Mizushima (2007) *Genes Dev.* 21:2861-73). To serve as a positive control, N2a cells were treated with rapamycin, a potent mTOR signaling inhibitor, and it was observed that rapamycin also increased the LC3-II/LC3-I ratio. To validate the western blot result, LC3 puncta were monitored in intact fixed cells using immunofluorescence microscopy. The result revealed that the number of the fluorescent LC3 puncta was significantly increased in N2a cells after K604 or rapamycin treatment. In addition to LC3, autophagy can be analyzed by monitoring p62 levels (Mizushima, et al. (2010) *Cell* 140:313-326). p62 is a selective autophagic substrate, and p62 protein levels inversely correlate with autophagic activity (Bjørkøy, et al. (2005) *J. Cell Biol.* 171:603-14). By western blot, it was observed that either K604 or rapamycin significantly decreased the levels of p62 in N2a cells. These results demonstrate that blocking ACAT1 by K604 increases autophagy in N2a cells.

CI-1011 is an isotype-nonspecific ACAT inhibitor that blocks both ACAT1 and ACAT2 with essentially the same efficacy (Ikenoya, et al. (2007) *Atherosclerosis* 191:290-7). Treating a mouse model for AD with CI-1011 reduced Aβ and amyloid plaque levels (Huttunen, et al. (2010) *J. Neuropathol. Exp. Neurol.* 69:777-788). To test if CI-1011 could also enhance autophagy in N2a cells, the efficacy of CI-1011 was first examined and it was found that ACAT activity was blocked in N2a cells in a dose-dependent manner. Consistent with a previous report (Ikenoya, et al. (2007) *Atherosclerosis* 191:290-7), when compared at several concentrations, CI-1011 was less efficient than K604 in inhibiting ACAT activity. LC3-II levels were subsequently analysed in N2a cells after treatment with CI-1011 at 5 μM. The result of a western blot showed that CI-1011 significantly increased the LC3-II level; the LC3-II level was further augmented by treating cells with NH$_4$Cl (to block lysosome activity). This result indicated that similar to K604, CI-1011 also increases autophagy flux without interfering with the clearance of autophagosome. Because CI-1011 inhibits both ACAT1 and ACAT2, K604 was used in the additional analysis herein to specifically study the effect of ACAT1 blockage in neuronal cells.

Inhibiting ACAT1 in N2a Cells Enhances Autophagy without Altering mTOR Signaling or Total Cellular Cholesterol Content.

As demonstrated herein, ACAT1 blockage in microglia increased autophagy in an mTOR-independent manner. To determine whether K604 enhances autophagy in N2a cells by inhibiting mTOR signaling, mTOR kinase activity was monitored by analyzing the levels of phosphorylation of its substrates, p70S6 kinase and 4E-BP1 in cells treated with or without K604. The result of the western blot analysis showed that K604 did not alter the phosphorylation levels of p70S6K or 4E-BP1. In contrast, rapamycin significantly inhibited phosphorylation of these substrates. These results showed that, similar to microglia, blocking ACAT1 by K604 increases autophagy in N2a cells by an mTOR-independent mechanism.

In various cell culture systems examined, cellular cholesterol levels are reported to affect autophagy in various manners (Cheng, et al. (2006) *Biochem. Biophys. Res. Commun.* 351:246-52; Xu, et al. (2010) *J. Lipid Res.* 51:2581-90; Ouimet, et al. (2011) *Cell Metab.* 13:655-67). As demonstrated herein with microglial cells, inhibiting ACAT1 by K604 enhanced autophagy without altering total cellular cholesterol (free cholesterol and cholesteryl ester) content. To test whether K604 may affect total cholesterol content in the N2a cells, free cholesterol and cholesteryl ester contents were examined with or without K604 treatment. The result showed that treating N2a cells with K604 for 24 hours decreased the cholesteryl ester content by approximately 50%, without affecting either the free cholesterol or the total cholesterol contents. This result indicates that similar to the result observed in microglial cells, in N2a cells, the mechanism by which ACAT1 blockage promotes autophagy is not by altering total cellular cholesterol contents in cells.

K604 Reduces Human Tau Protein Content Ectopically Expressed in N2a Cells.

It has been shown that in N2a cells and in rat primary neurons, enhancing autophagy by using trehalose, an mTOR-independent enhancer of autophagy, promotes degradation of human tau ectopically expressed in these cells (Krüger, et al. (2012) Neurobiol. Aging 33:2291-2305). Since K604 promotes autophagy in N2a cells, it was determined whether K604 could promote human tau degradation in N2a cells. To test this possibility, human wild type-tau (WT-tau) or human mutant tau (P301L-tau) was expressed in N2a cells by transient transfection, and the effects of K604 on tau levels were examined. The result of the western blot analysis showed that K604 decreased the levels of both WT-tau and P301L-tau in a dose-dependent manner. In western blot analysis, the human tau protein was detected as multiple bands, presumably because of phosphorylations at multiple sites within tau (Matsumura, et al. (1999) Am. J. Pathol. 154:1649-56; Sontag, et al. (1996) Neuron 17:1201-7). The result of a control experiment showed that rapamycin also reduced both the WT-tau and P301L-tau levels in these cells. These data indicated that augmenting autophagy either by K604 or by rapamycin stimulated human tau degradation. N2a cells express endogenous mouse tau. Endogenous mouse tau was monitored using the antibody Tau-5 and this analysis showed that in N2a cells, the endogenous tau protein content was not affected by K604 treatment.

K604 Reduces Human Tau Protein Content in N2a Cells Via Augmented Autophagy.

The results described above indicate that K604 decreases human tau protein content by increasing autophagy. Atg5 is an essential protein for autophagosome formation (Mizushima, et al. (2001) J. Cell Biol. 152:657-68). Atg5 KD in N2a cells that transiently express P301L-tau was performed. A negative control experiment was carried out using a control siRNA (Ctrl KD). Afterwards, the effect of K604 on P301L-tau levels in Atg5 KD cells was compared to Ctrl KD cells. Rapamycin treatment was also included as a positive control to promote the mTOR-dependent autophagy. The results showed that Atg5 KD diminished the Atg5 protein levels by approximately 90%, and dramatically reduced the LC3-II levels. In contrast to the result obtained in Ctrl cells, in Atg5 KD cells, neither rapamycin nor K604 was able to increase the residual LC3-II levels. It was also observed that, when compared to Ctrl KD, Atg5 KD significantly increased the P301L-tau levels; after Atg5 KD, neither K604 nor rapamycin was able to reduce the P301L-tau levels. These data demonstrate that after autophagy is attenuated by Atg5 KD, similar to rapamycin, K604 is no longer able to reduce P301L-tau content in N2a cells. 3-methyladenine (3MA) is a class III PI3-kinase inhibitor; treating cells with 3MA effectively inhibits autophagy (Mizushima, et al. (2010) Cell 140:313-326). N2a cells were also treated with 3MA and it was found that, similar to the effect of Atg5 KD, 3MA significantly increased the mutant tau level and abolished the effect of K604 on P301L-tau. Together, these results demonstrate that in N2a cells, K604 decreases P301L-tau via increased autophagy.

Acat1 KO Decreases P301L-Tau Protein Content by Increasing Autophagosome Formation in AD Neurons.

Figure 5A:
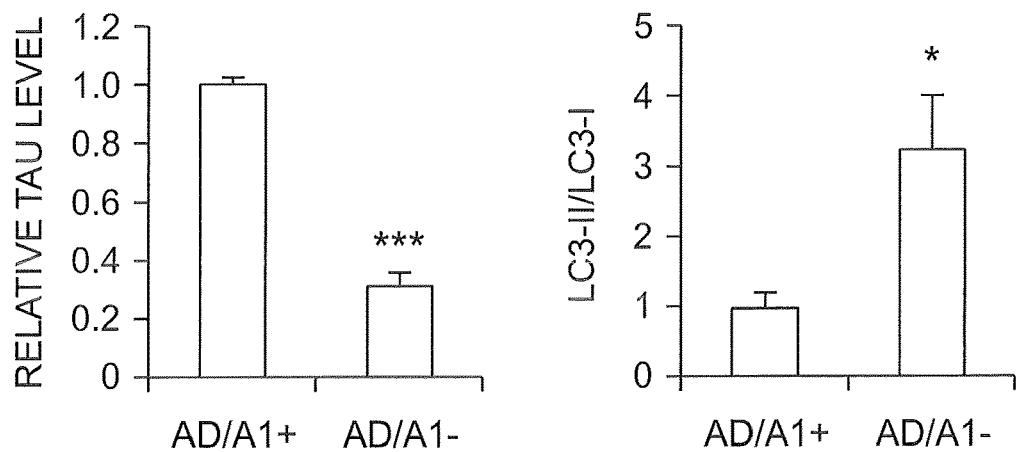
FIG. 5A shows that Acat1 knockout (KO) in AD neurons promotes P301L-Tau degradation by increasing autophagy. Primary cortical neurons were isolated from neonatal 3xTg-AD mice with Acat1 (AD/A1+) or without Acat1 (AD/A1−) mice. P301L-Tau and LC3 levels in primary cortical neurons were analyzed by western blot. (n=3, *p<0.05, ***p<0.001).

N2a is a fast-growing mouse neuroblastoma cell line. It was determined whether genetic inactivation of ACAT1 in primary neurons could elicit the same effects as what the ACAT1 inhibitor K604 did in N2a cells. The 3×Tg-AD mouse expresses human mutant P301L-tau (Oddo, et al. (2003) Neuron 39:409-21). Primary cortical neurons were isolated from neonatal 3×Tg-AD mice with Acat1 (AD/A1+) or without Acat1 (AD/A1−) and P301L-tau levels and autophagosome formation were analyzed. The results showed that when compared to AD/A1+ neurons, in AD/A1− neurons, the P301L-tau levels were decreased by approximately 70%, whereas the LC3-II/LC3-I ratio was increased by about 3-fold (FIG. 5A). The result of a quantitative PCR (qPCR) experiment showed that the mRNA levels of human mutant tau were comparable between AD/A1+ and AD/A1− neurons, demonstrating that in AD neurons, Acat1 KO reduces the protein level without affecting the mRNA level of P301L-tau. Autophagy can be activated as a consequence of endoplasmic reticulum stress (Ogata, et al. (2006) Mol. Cell. Biol. 26:9220-31). As demonstrated herein with microglia, ACAT1 blockage increased autophagy without inducing endoplasmic reticulum stress. The protein content of GRP78/BiP has been used as a protein marker to monitor ER stress; its level is increased upon endoplasmic reticulum stress (Harding, et al. (2002) Annu. Rev. Cell Dev. Biol. 18:575-99). GRP78/BiP content was monitored by western blot, and the results indicates that GRP78/BiP levels were the same between AD/A1+ and AD/A1− neurons. These results show that similar to what was shown in microglia, in cortical neurons, Acat1 KO enhances autophagy without altering endoplasmic reticulum stress response.

The transcription factor EB (TFEB) regulates lysosome biogenesis by increasing transcription of multiple target genes (Sardiello, et al. (2009) Science 325:473-7). In cultured microglia and in adult microglia freshly isolated from 3×Tg-AD mice, ACAT1 blockage increases the expressions of various TFEB-target genes. To investigate whether Acat1 KO increases lysosome biogenesis in AD neurons, mRNAs from AD/A1+ or AD/A1− cortical neurons were isolated and qPCR analysis was performed. The results showed that Acat1 KO increased the expression levels of four different TFEB-target genes; the result of a control experiment showed that Acat1 KO did not alter the expression of a house keeping enzyme hypoxanthine-guanine phosphoribosyltransferase (HPRT). These data demonstrate that in AD neurons, Acat1 KO stimulates TFEB-mediated lysosome biogenesis.

K604 Stimulates Autophagy, Increases Cellular Acidic Compartments, and Decreases P301L-Tau Content in AD Neurons.

Figure 5B:
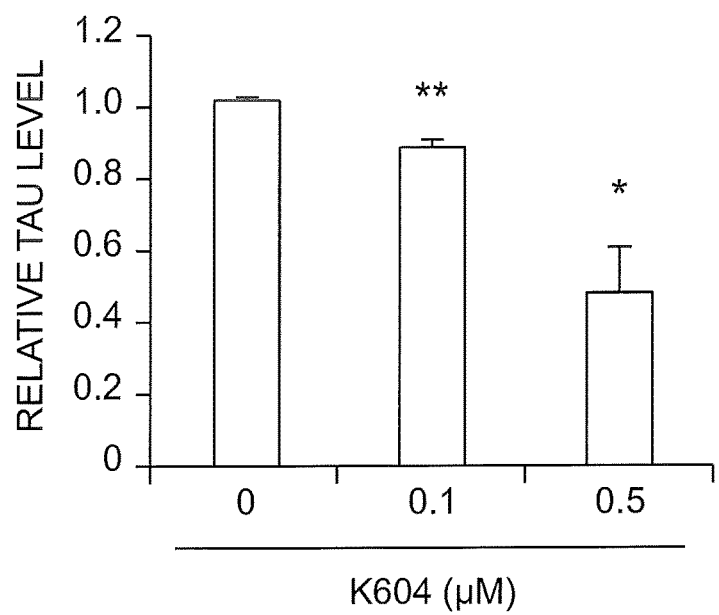
FIG. 5B shows that K604 stimulates autophagy-mediated proteolysis and increases P301LTau degradation in AD neurons. AD/A1+ cortical neurons were treated with the indicated concentrations of K604 for 24 hours. P301L-Tau and LC3 levels were analyzed by western blot. (n=2, *p<0.05, **p<0.01).

As demonstrated herein, K604 reduces P301L-tau levels in N2a cells. To examine whether K604 can reduce P301L-tau levels in primary neurons, AD/A1+ cortical neurons were treated with K604 at the indicated concentrations for 24 hours and the levels of P301L-tau and LC3 were analyzed by western blot. The results showed that similar to what was shown in N2a cells, K604 reduced P301L-tau levels (FIG. 5B) and increased LC3-II levels; the dose-dependency of the K604 effects in primary neurons and in N2a cells were similar. In microglia, ACAT1 blockage stimulated lysosomal proteolysis and increased cellular acidic compartments (i.e., late endosomes/lysosomes); this increase was demonstrated by using flow cytometry after cells were stained with the dye LYSOTRACKER. To examine whether K604 causes the same effect in neurons, AD/A1+ cortical neurons were treated with K604 at 0.5 µM for various amounts of time as indicated, and estimated cellular acidic compartments. The result revealed that treating the AD/A1+ cortical neurons with K604 for 8 to hours significantly increased the LYSOTRACKER-positive compartments. Together, these results demonstrate that similar to the effects of Acat1 KO in AD neurons, the ACAT1-specific inhibitor K604 stimulates autophagy-mediated lysosomal proteolysis and decreases P301L-tau content in AD neurons.

Acat1 KO Decreases P301L-tau Levels in the Brains of Young AD Mice but not in Old AD Mice.

The physiological significance of these findings in N2a cells and in cortical neurons was tested by monitoring the P301L-tau levels in the brains of AD mice with or without Acat1. Brain samples were prepared in 10% sodium dodecyl sulfate (SDS) from age-matched male AD/A1+ and AD/A1− mice, and tau protein content was analyzed in the brain homogenates by western blot. P301L-tau levels were first monitored using the human tau specific antibody HT7. The results showed that, when compared with the AD/A1+ mice, at 2 and 4 months of age, the AD/A1− mice contained significantly less P301L-tau. Subsequently, the endogenous mouse tau was monitored in the brains of WT and Acat1 KO mice. The result showed that at 4 months of age, Acat1 KO did not alter the endogenous tau levels.

The AT8 antibody, which specifically recognizes the phosphorylated tau at Ser202/Thr205, was then used to monitor phosphorylation of P301L-tau. In the 3×Tg-AD mouse model, Ser202/Thr205-specific hyperphosphorylation of P301L-tau becomes apparent between 12 to 15 months of ages (Oddo, et al. (2003) *Neuron* 39:409-21). The phosphorylated P301L-tau levels in the AD/A1+ and the AD/A1− mice were compared at 2 or 21 months of age using the AT8 antibody. The result showed that at 2 months of age, no AT8-specific phosphorylation was detectable in these mice, while at 21 months of age, highly significant levels of AT8-specific phosphorylation occurred in both types of these mice. The levels of total P301L-tau and phosphorylated P301L-tau were subsequently compared in the old AD/A1+ and AD/A1− mice. The result showed that at 17 and 21 months of age, for both total P301L-tau and hyperphosphorylated P301L-tau, comparable levels were present in the brains of AD/A1+ and AD/A1− mice. The number of NFTs in the hippocampi of AD mice at 17 months of age was examined and it was observed that no significant difference in NFTs existed between AD/A1+ and AD/A1− mice. The results showed that Acat1 KO was effective in reducing total P301L-tau in young AD mice but not in old AD mice. These results raised the possibility that Acat1 KO in AD mice might increase autophagy in young AD mice only. To test this possibility, the LC3II/LC3I ratio was monitored in the brain homogenates of AD/A1+ and AD/A1− mice at 2 months and at 21 months of age. The result showed that at both ages, the AD/A1− mice exhibited significantly increased LC3II/LC3I ratio in their brains than the AD/A1+ mice. This result demonstrates that the inability of Acat1 KO in reducing P301L-tau in old AD mice is not because Acat1 KO is unable to increase autophagosome in these mice.

What is claimed is:

1. A method for stimulating clearance of misfolded or aggregated proteins and peptides in microglia or neurons comprising administering to a subject in need thereof an Acyl-CoA: Cholesterol Acyltransferase 1 (ACAT1)-selective inhibitor thereby stimulating clearance of the misfolded or aggregated proteins and peptides in microglia or neurons in the subject, wherein the ACAT1-selective inhibitor is a compound having the structure:

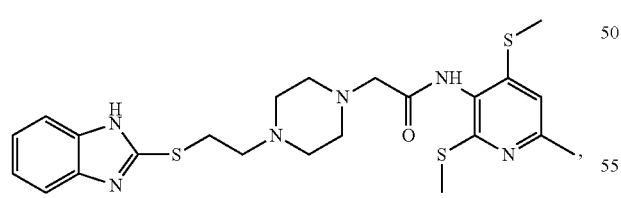

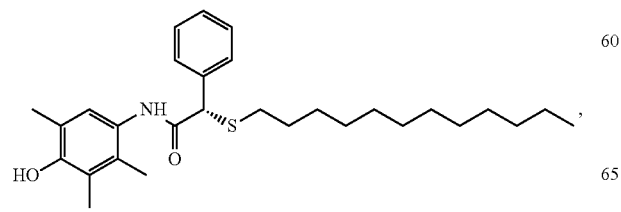

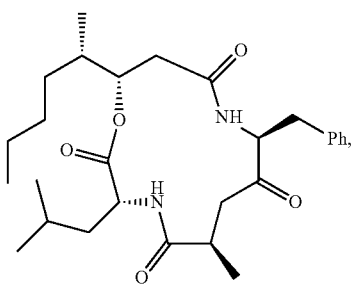

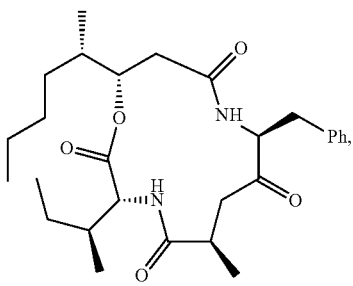

-continued

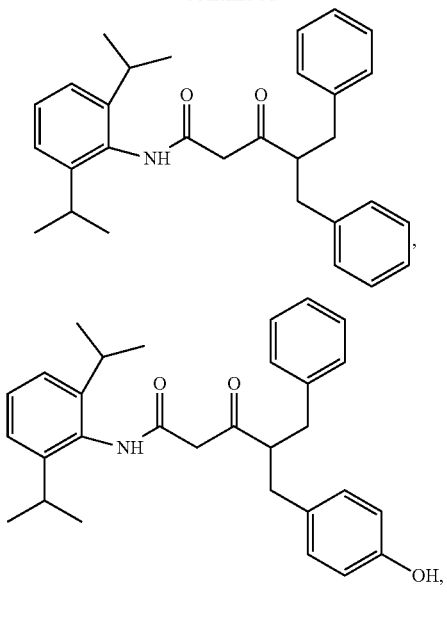

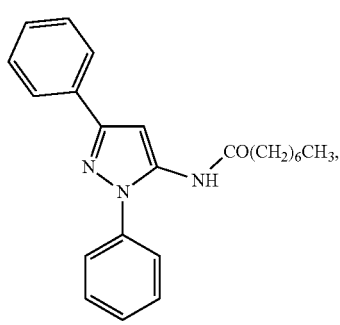

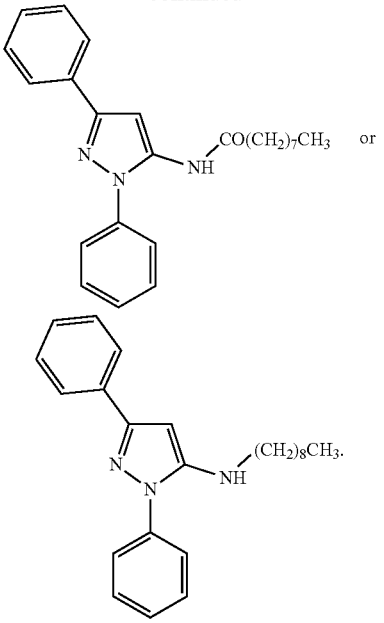

2. The method of claim 1, wherein the inhibitor has an $IC_{50}$ value for Acyl-CoA: Cholesterol Acyltransferase 1 which is at least twice the corresponding $IC_{50}$ value for Acyl-CoA: Cholesterol Acyltransferase 2.

3. The method of claim 1, wherein the inhibitor inhibits the expression or activity of Acyl-CoA: Cholesterol Acyltransferase 1.

4. The method of claim 1, wherein the inhibitor has an $IC_{50}$ value in the range of 1 nM to 100 μM.

5. The method of claim 1, wherein the inhibitor is administered intranasally, intrathecally, or directly to the brain of the subject by a shunt or a catheter.

6. The method of claim 1, wherein the inhibitor is encapsulated in an exosome or liposome.

7. The method of claim 6, wherein the exosome or liposome is modified with a brain-targeting moiety.

8. The method of claim 1, wherein the proteins are amyloid beta proteins.

9. A method for treating a neurodegenerative disease associated with accumulation of misfolded or aggregated proteins or peptides in microglia or neurons of brain tissue comprising administering to a subject in need thereof an Acyl-CoA: Cholesterol Acyltransferase 1 (ACAT1)-selective inhibitor thereby decreasing the accumulation of misfolded or aggregated proteins or peptides in microglia or neurons of brain tissue in the subject, thereby treating the neurodegenerative disease, wherein the ACAT1-selective inhibitor is a compound having the structure:

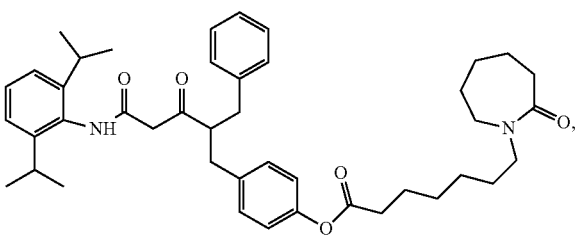

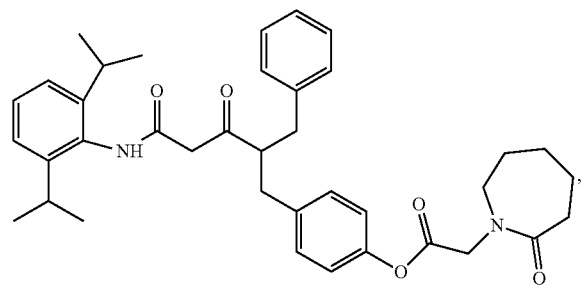

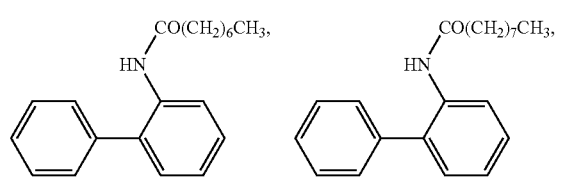

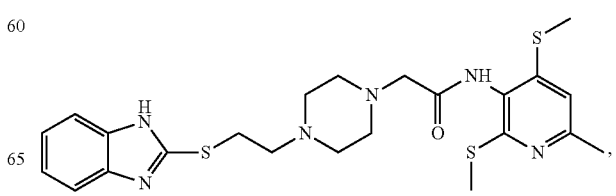

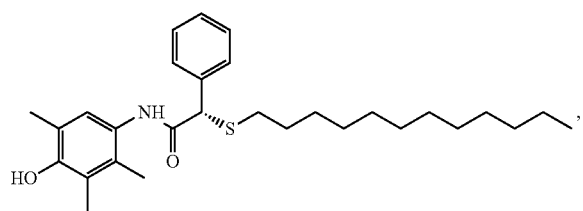

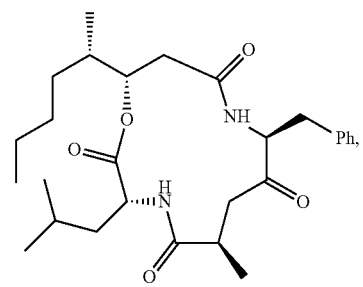

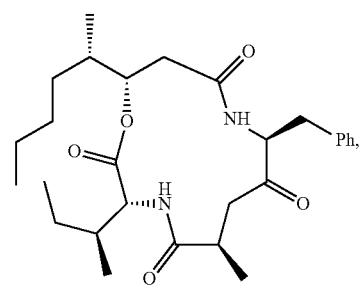

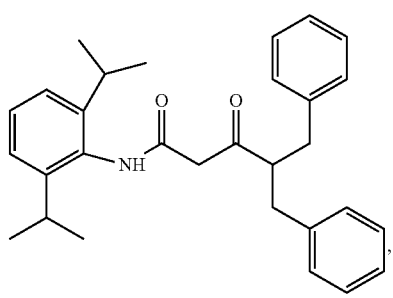

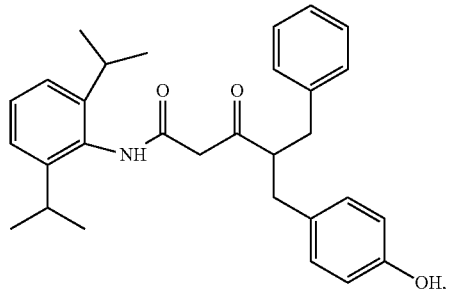

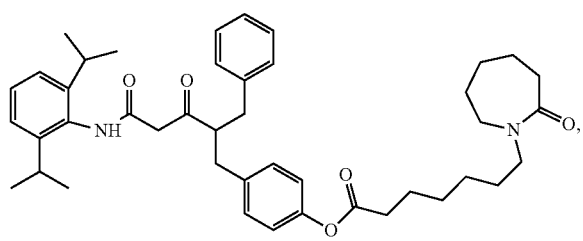

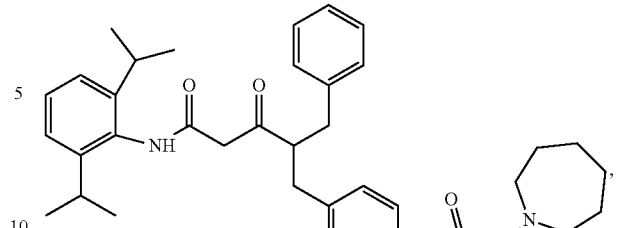

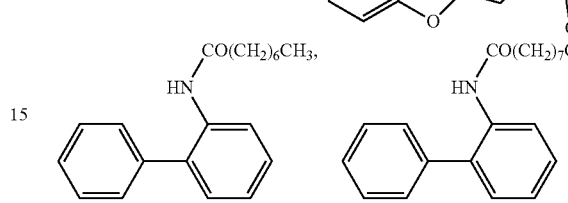

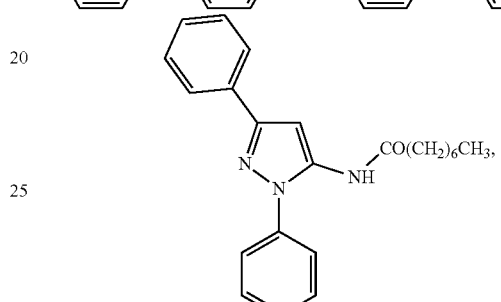

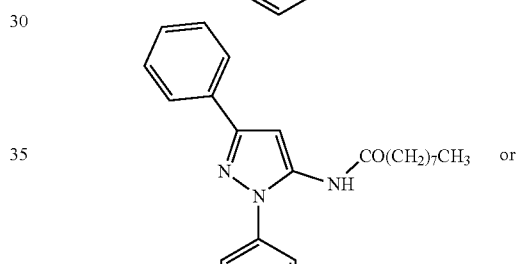

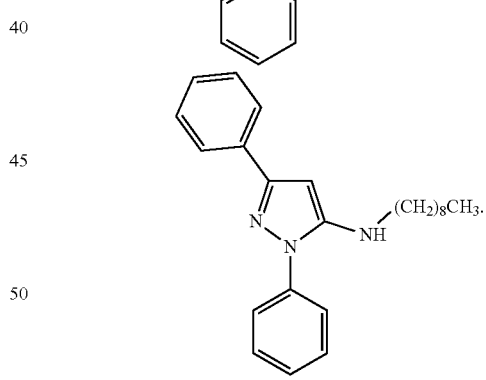

10. The method of claim 9, wherein the neurodegenerative disease is Alzheimer's disease, tauopathy, frontotemporal dementia, Parkinson's disease, Huntington Disease, or amylotrophic lateral sclerosis.

11. The method of claim 9, wherein the inhibitor has an $IC_{50}$ value for Acyl-CoA: Cholesterol Acyltransferase 1 which is at least twice the corresponding $IC_{50}$ value for Acyl-CoA: Cholesterol Acyltransferase 2.

12. The method of claim 9, wherein the inhibitor inhibits the expression or activity of Acyl-CoA: Cholesterol Acyltransferase 1.

13. The method of claim 9, wherein the inhibitor has an $IC_{50}$ value in the range of 1 nM to 100 μM.

14. The method of claim 9, wherein the inhibitor is administered intranasally, intrathecally, or directly to the brain of the subject by a shunt or a catheter.

15. The method of claim 9, wherein the inhibitor is encapsulated in an exosome or liposome.

16. The method of claim 15, wherein the exosome or liposome is modified with a targeting moiety.

\* \* \* \* \*